(12) United States Patent
Fey

(10) Patent No.: US 8,802,847 B2
(45) Date of Patent: *Aug. 12, 2014

(54) PROCESS FOR PREPARING SUBSTITUTED 5-FLUORO-1H-PYRAZOLOPYRIDINES

(71) Applicant: Bayer Intellectual Property GmbH, Monheim (DE)

(72) Inventor: Peter Fey, Wuppertal (DE)

(73) Assignee: Bayer Intellectual Property GmbH, Monheim (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/684,670

(22) Filed: Nov. 26, 2012

(65) Prior Publication Data
US 2013/0143900 A1  Jun. 6, 2013

(30) Foreign Application Priority Data

Nov. 25, 2011 (EP) .................................... 11190789
Dec. 7, 2011 (EP) .................................... 11192301

(51) Int. Cl.
C07D 295/18 (2006.01)

(52) U.S. Cl.
USPC .......................................... 544/175; 544/328

(58) Field of Classification Search
USPC ................................................ 544/175, 328
See application file for complete search history.

(56) References Cited

U.S. PATENT DOCUMENTS

| | | | |
|---|---|---|---|
| 6,166,027 A | 12/2000 | Straub et al. | |
| 6,180,656 B1 | 1/2001 | Furstner et al. | |
| 6,451,805 B1 | 9/2002 | Straub et al. | |
| 6,693,102 B2 | 2/2004 | Stasch et al. | |
| 6,743,798 B1 | 6/2004 | Straub et al. | |
| 6,833,364 B1 | 12/2004 | Straub et al. | |
| 6,903,089 B1 | 6/2005 | Stasch et al. | |
| 6,919,345 B2 | 7/2005 | Stasch et al. | |
| 7,105,523 B2 | 9/2006 | Stasch et al. | |
| 7,115,599 B2 | 10/2006 | Stasch et al. | |
| 7,135,474 B2 | 11/2006 | Weigland et al. | |
| 7,173,037 B2 | 2/2007 | Alonso-Alija et al. | |
| 7,410,973 B2 | 8/2008 | Fuerer et al. | |
| 8,242,272 B2 | 8/2012 | Jimenez et al. | |
| 8,309,551 B2 | 11/2012 | Schirok et al. | |
| 8,420,656 B2 * | 4/2013 | Follmann et al. | 514/256 |
| 8,492,544 B2 | 7/2013 | Mais et al. | |
| 8,501,945 B2 | 8/2013 | Mais et al. | |
| 2004/0235863 A1 | 11/2004 | Feurer et al. | |
| 2006/0167016 A1 | 7/2006 | Fuerer et al. | |
| 2007/0225299 A1 | 9/2007 | Bischoff et al. | |

(Continued)

FOREIGN PATENT DOCUMENTS

| | | |
|---|---|---|
| CA | 2346698 | 4/2000 |
| CA | 2809911 | 3/2012 |
| EP | 0463756 | 4/1995 |
| WO | 0006567 | 2/2000 |

OTHER PUBLICATIONS

Barraclough et al.,"Mono-aroylation of 2,3- and 3,4-Diaminopyridine and 4,5-Diaminopyrimidine, and Syntheses of Putative Inotrope/β-Adrenoceptor Antagonists," J. Chem. Res., 1996, 9: 2316-2335.

(Continued)

*Primary Examiner* — Rei-tsang Shiao
(74) *Attorney, Agent, or Firm* — Karen B. King

(57) ABSTRACT

The present application relates to a novel and efficient process for preparing novel substituted 5-fluoro-1H-pyrazolopyridines of the formula (VI)

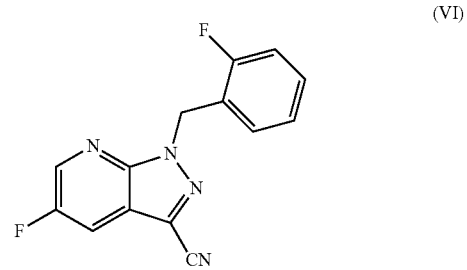

(VI)

which are suitable as an intermediate for production of medicaments and for production of medicaments for treatment and/or prophylaxis of cardiovascular disorders. More particularly, the 5-fluoro-1H-pyrazolopyridines of the formula (VI) are suitable for preparation of the compound of the formula (I)

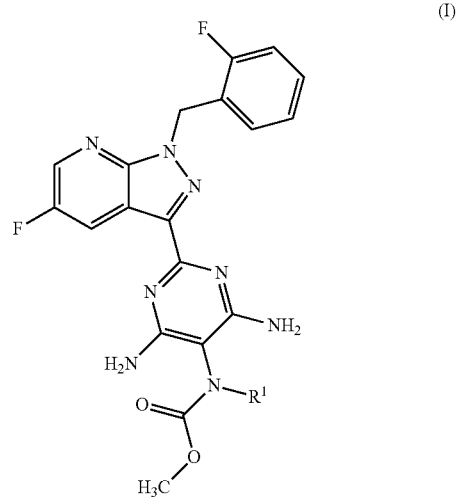

(I)

which serves for production of medicaments, for production of medicaments for treatment and/or prophylaxis of cardiovascular disorders.

2 Claims, 14 Drawing Sheets

(56) References Cited

U.S. PATENT DOCUMENTS

| | | |
|---|---|---|
| 2011/0224197 A1 | 9/2011 | Henkel et al. |
| 2012/0029002 A1 | 2/2012 | Straub et al. |
| 2013/0178475 A1 | 7/2013 | Moore et al. |
| 2013/0211090 A1 | 8/2013 | Follmann et al. |
| 2013/0267548 A1 | 10/2013 | Follmann et al. |

OTHER PUBLICATIONS

Cavalieri et al.,"A Synthesis of Adenine: The Incorporation of Isotopes of Nitrogen and Carbon," J. Am. Chem. Soc., Feb. 1949, 71:533-536.

Cheng et al.,"Potential Purine Antagonists VII. Synthesis of 6-Alkylpyrazolo-[3,4-d]pyrimidines," J. Org. Chem., 1958, 23:191-200.

Evans et al.,"The Preparation of 4-Amino- and Other Pteridines," J. of Chem. Soc., 1956, pp. 4106-4113.

Goldberg et al., "Stimulation of Human Platelet Guanylate Cyclase by Fatty Acids," J. Biol. Chem., 1977, 252, 1279-1285.

Hughes,"Progress in the Mitsunobu Reaction. A Review," Org. Prep. Procedures Int., 1996, 28(2):127-164.

Ko et al., "YC-1, a Novel Activator of Platelet Guanylate Cyclase," Blood, Dec. 1994, 84(12): 4226-4233.

Li et al., "Synthesis and Structure-Activity Relationships of 2-Pyridones: A Novel Series of Potent DNA Gyrase Inhibitors as Antibacterial Agents," J. Med. Chem., 1996, 39: 3070-3088.

Markovski et al., "Reactions of Pentakis(2,2,3,3-Tetrafluoropropoxy) Phosphorane with Secondary Amines," Zhurnal Obshchei Khimii 1980, 50(4):826-834.

Mittendorf et al., "Discovery of Riociguat (BAY 63-2521): A Potent, Oral Stimulator of Soluble Guanylate Cyclase for the Treatment of Pulmonary Hypertension," Chem. Med. Chem., 2009, 4: 853-865.

Mülsch et al., "Effect of YC-1, an NO-independent, superoxide-sensitive stimulator of soluble guanylyl cyclase, on smooth muscle responsiveness to nitrovasodilators," Brit. J. Pharm., 1997, 120: 681-689.

Pettibone et al., "A Structurally Novel Stimulator of Guanylate Cyclase with Long-Lasting Hypotensive Activity in the Dog," Euro. J. of Pharmacology, 1985, 116: 307-312.

Schwoch et al., "189. 2-3-Dihydrospirol [1H-4 and 5-azabenzimidazole-2,1'-cyclohexane](=Spiro[cyclohexane-1,2'(3'H)-1'H-imidazo[4,5-hb]pyridine] and Spiro[cyclohexane-1,2'(3'H)-1'H-imidazo[4,5-c[pyridine]): Reactions with Nucleophiles," Helvetia Chimica Acta, 1994, 77: 2175-2190.

Stasch et al., "Soluble Guanylate Cyclase as an Emerging Therapeutic Target in Cardiopulmonary Disease," Circulation, May 2011, 123: 2263-2273.

Winn et al., "2-(Alkylamino)nicotinic Acid and Analogs. Potent Angiotensin II Antagonists," J. Med. Chem 1993, 36: 2676-2688.

Yamanaka et al., "A New Facile and Efficient Method for the Preparation of (Z)-α-Fluoro-β-(dialkylamino) acrylaldehydes from (Polyfluoro-1-propenyl)trimethylammonium Iodide," Synlett, May 1993, 353-354.

Yamanaka et al., "Reactions of Polyfluoroalkyl o-Nitrobenzenesulfonates with Tertiary Amines," Nippon Kagaku Kaishi 1985, 10: 1988-1994 (in JP+abstract).

Yamanaka et al., "Synthesis and Reactions of (1H, 1H, αH-Perfluoroalkyl)-trimethylammonium Halides," Nippon Kagaku Kaishi, 1988, 7: 1036-1043 (in JP+abstract).

Yu et al., "Vasorelaxant Effect of Isoliquiritigenin, a novel soluble guanylate cyclase activator, in rat aorta," Brit. J. of Pharmacology, 1995, 114: 1587-1594.

U.S. Appl. No. 12/954,961, filed Nov. 29, 2011.
U.S. Appl. No. 13/111,856, filed May 19, 2011.
U.S. Appl. No. 13/882,123, 2013.
U.S. Appl. No. 13/851,373, published as 20120022084, 2012.
U.S. Appl. No. 13/819,905, published as 20130211090, 2013.
U.S. Appl. No. 13/882,118, published as 20130267548, 2013.

\* cited by examiner

FIG 1: IR spectra of the compound of the formula I in polymorph I, II and III
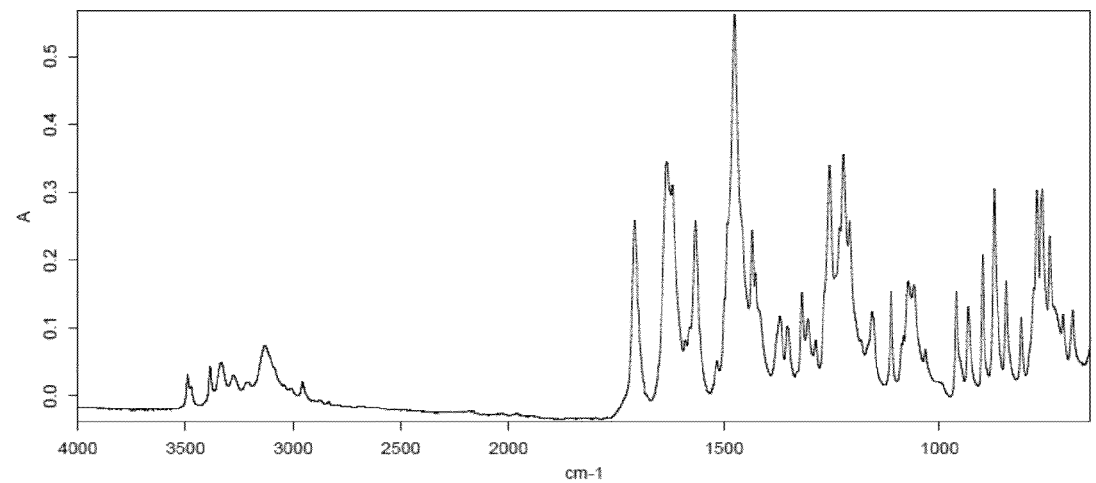
Polymorph I
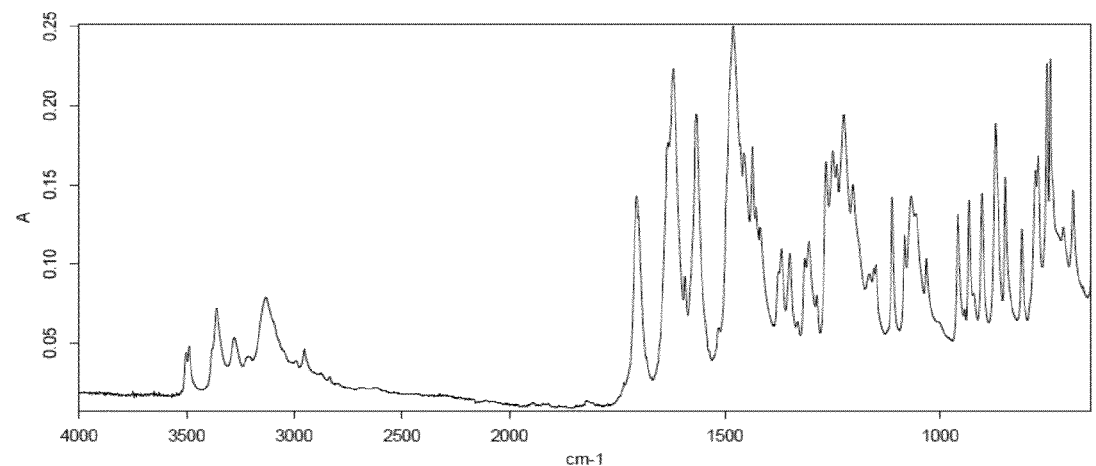
Polymorph II
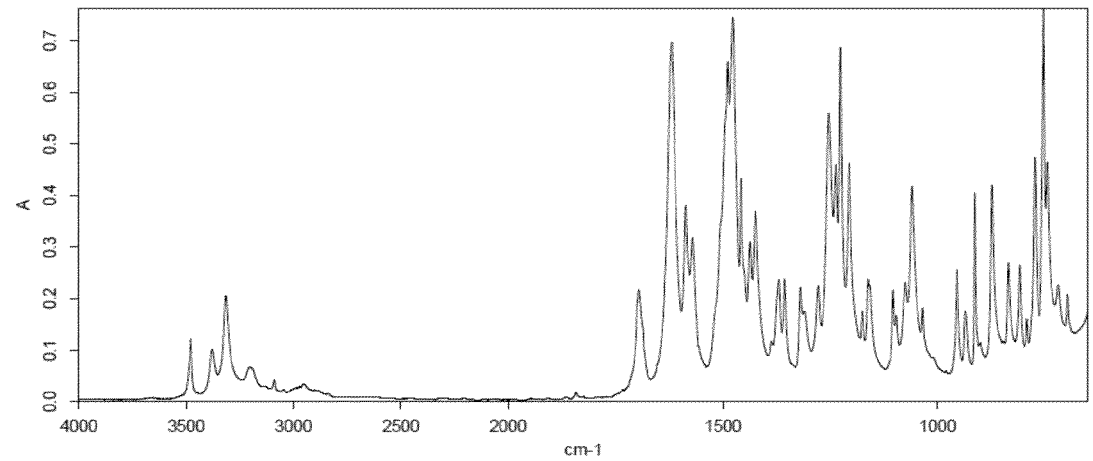
Polymorph III

FIG 2: IR spectra of the compound of the formula I in polymorph IV, V and of the triacetic acid solvate
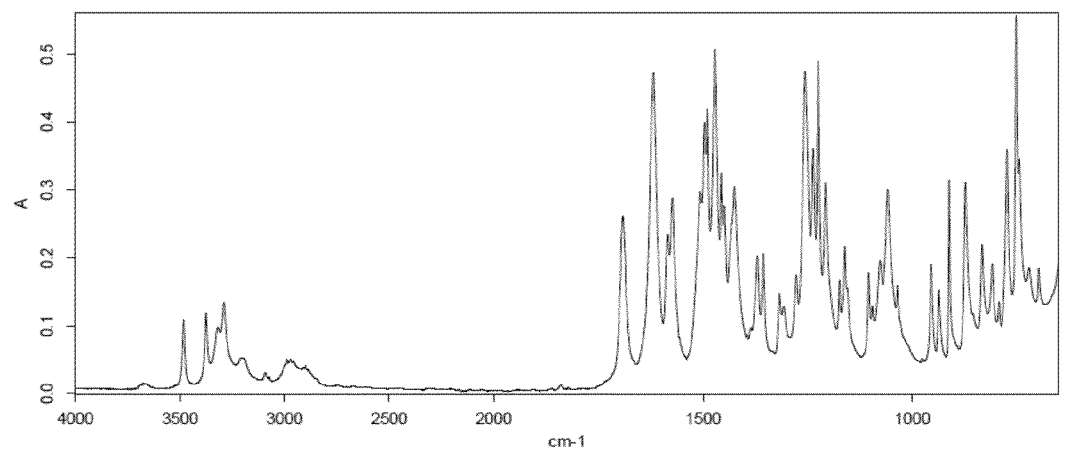
Polymorph IV
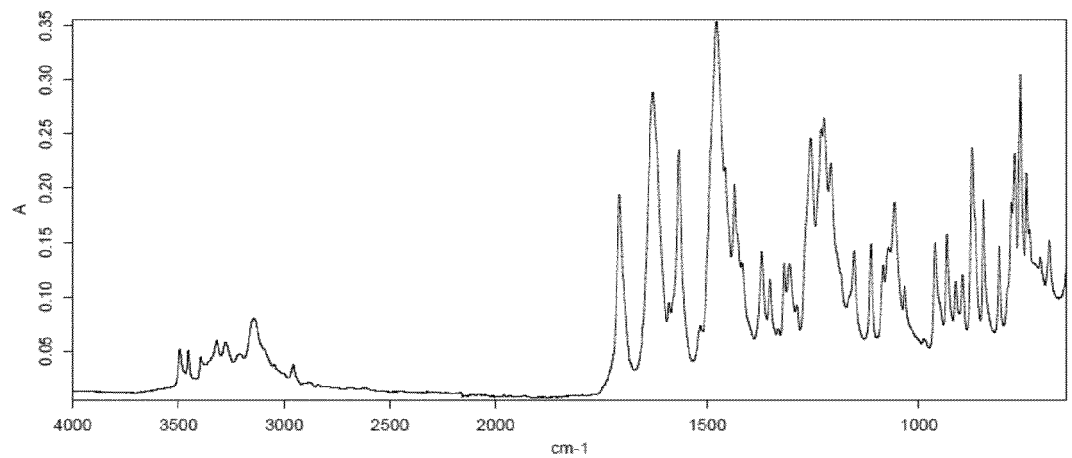
Polymorph V
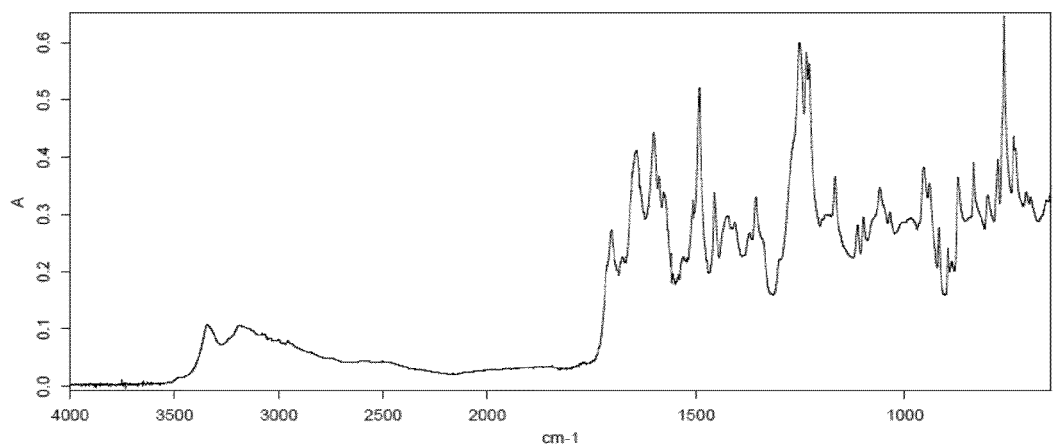
Triacetic acid solvate FIG 3: IR spectra of the compound of the formula I as the di-DMSO solvate, DMF/water solvate and the monohydrate
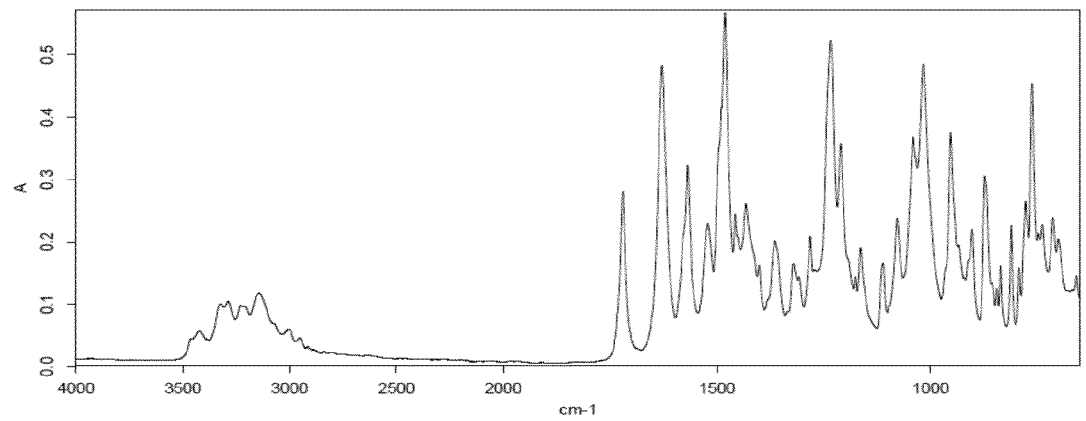
Di-DMSO solvate
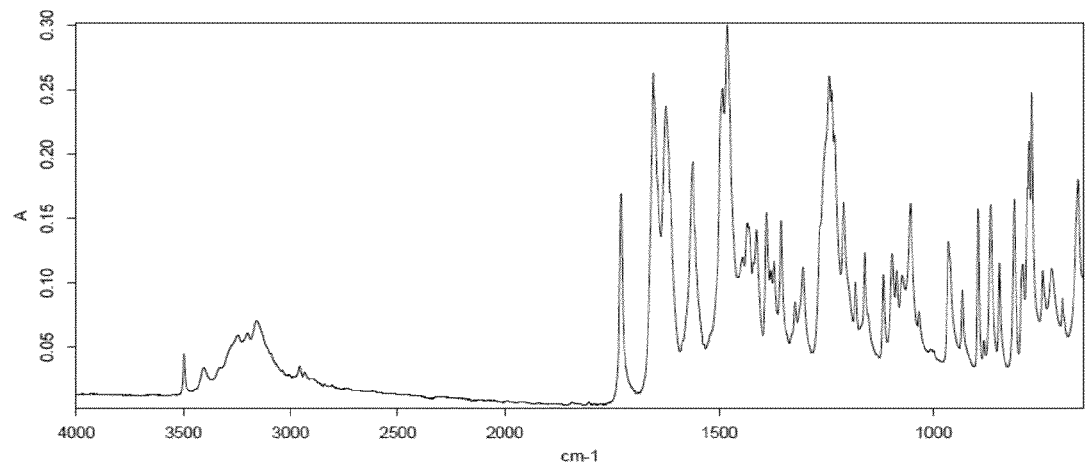
DMF/water solvate
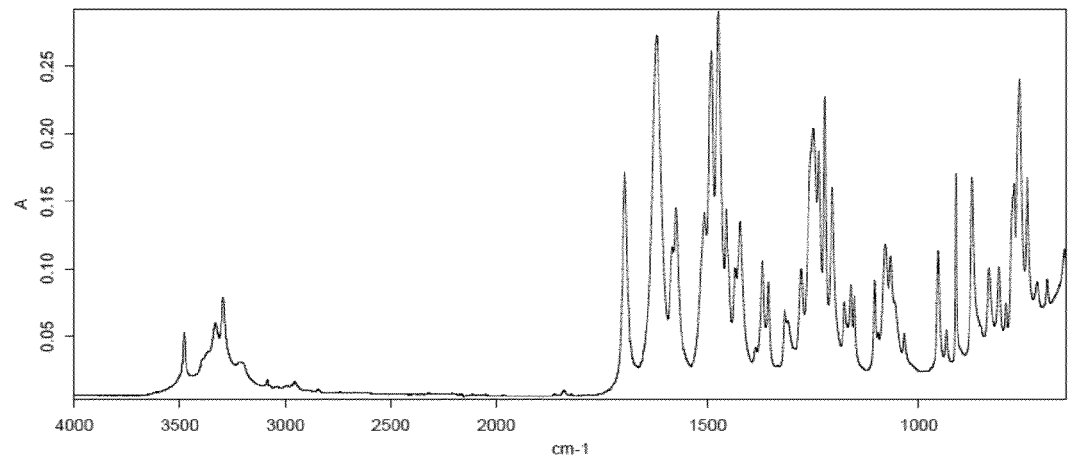
Monohydrate FIG 4: IR spectra of the compound of the formula I as the dihydrate
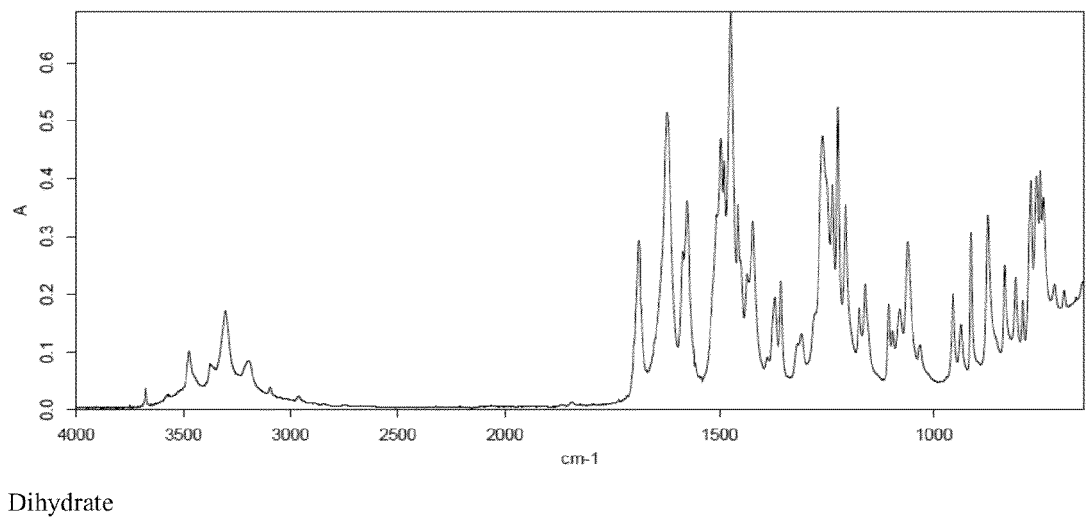
Dihydrate

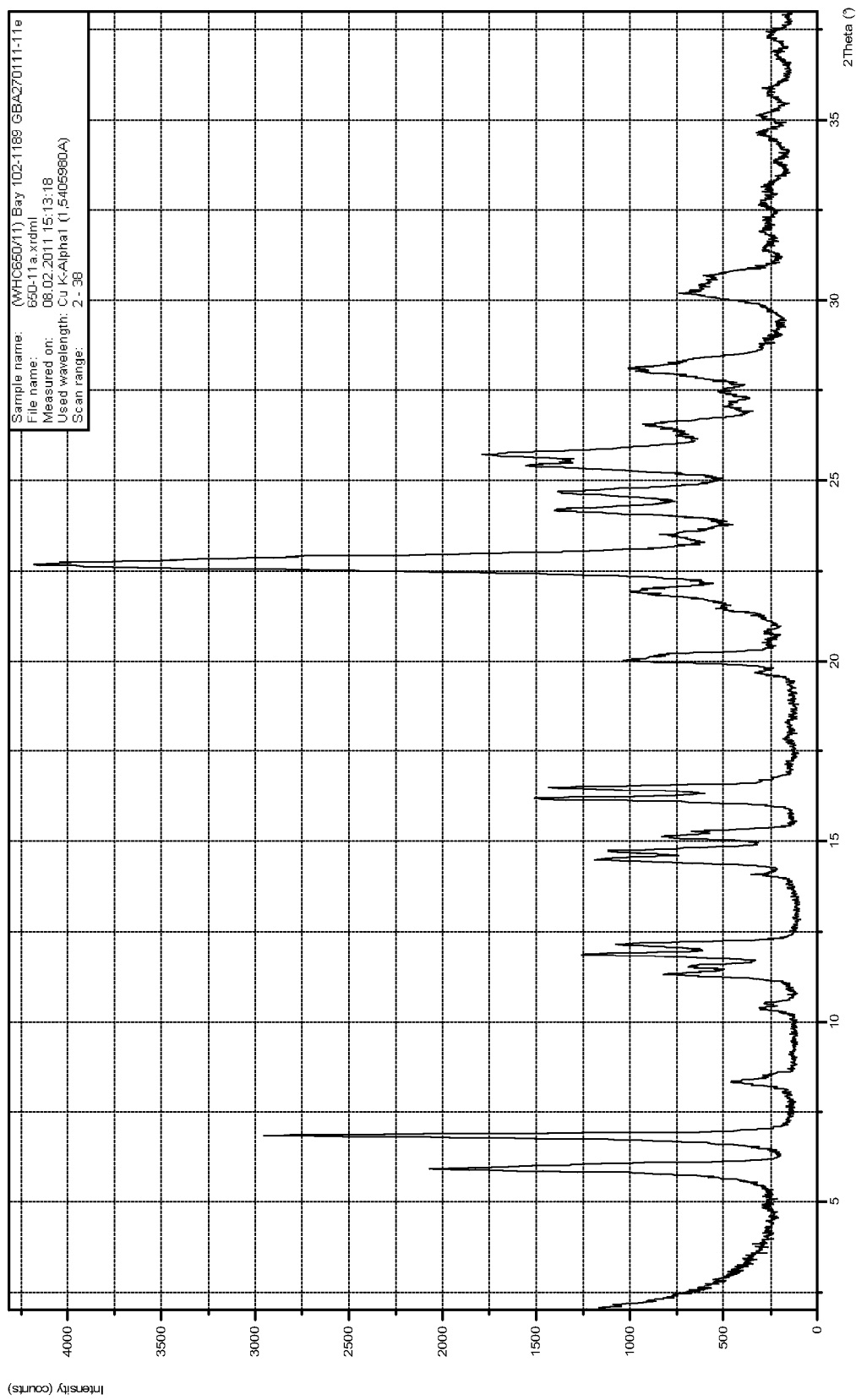
FIG 5: X-ray powder diffractograms of the compound of the formula I in polymorph I

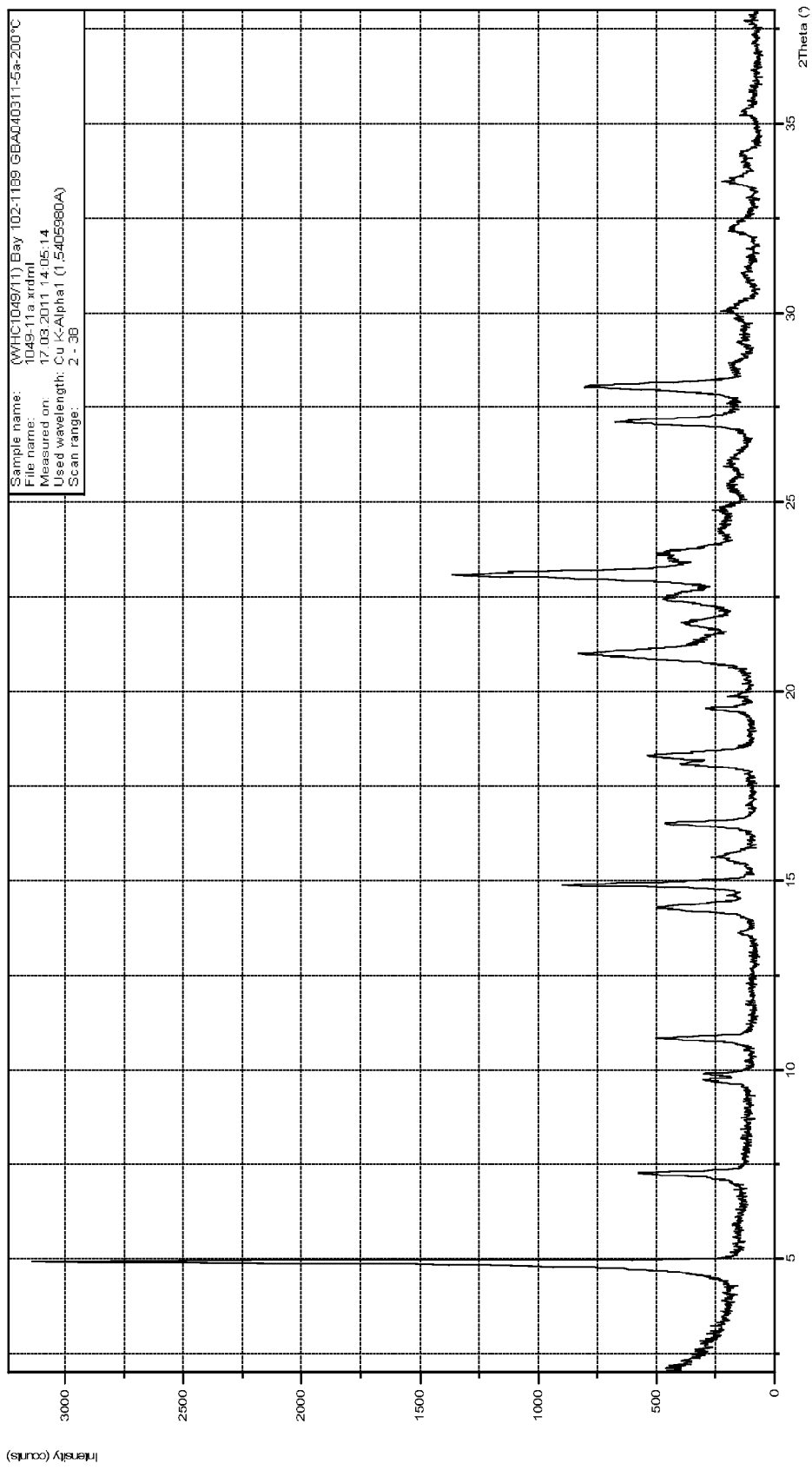
FIG 6: X-ray powder diffractograms of the compound of the formula I in polymorph II

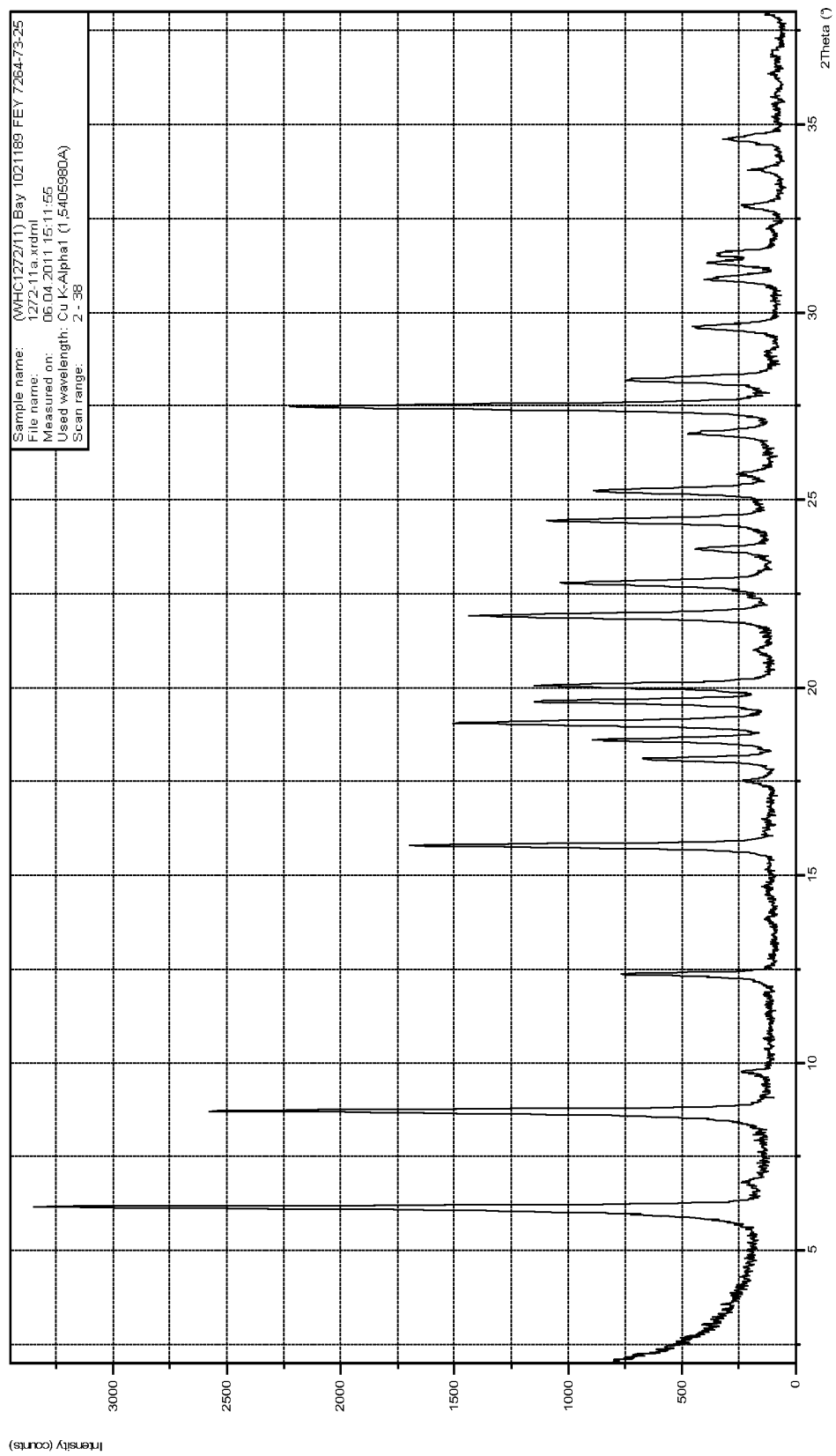
FIG 7: X-ray powder diffractograms of the compound of the formula I in polymorph III

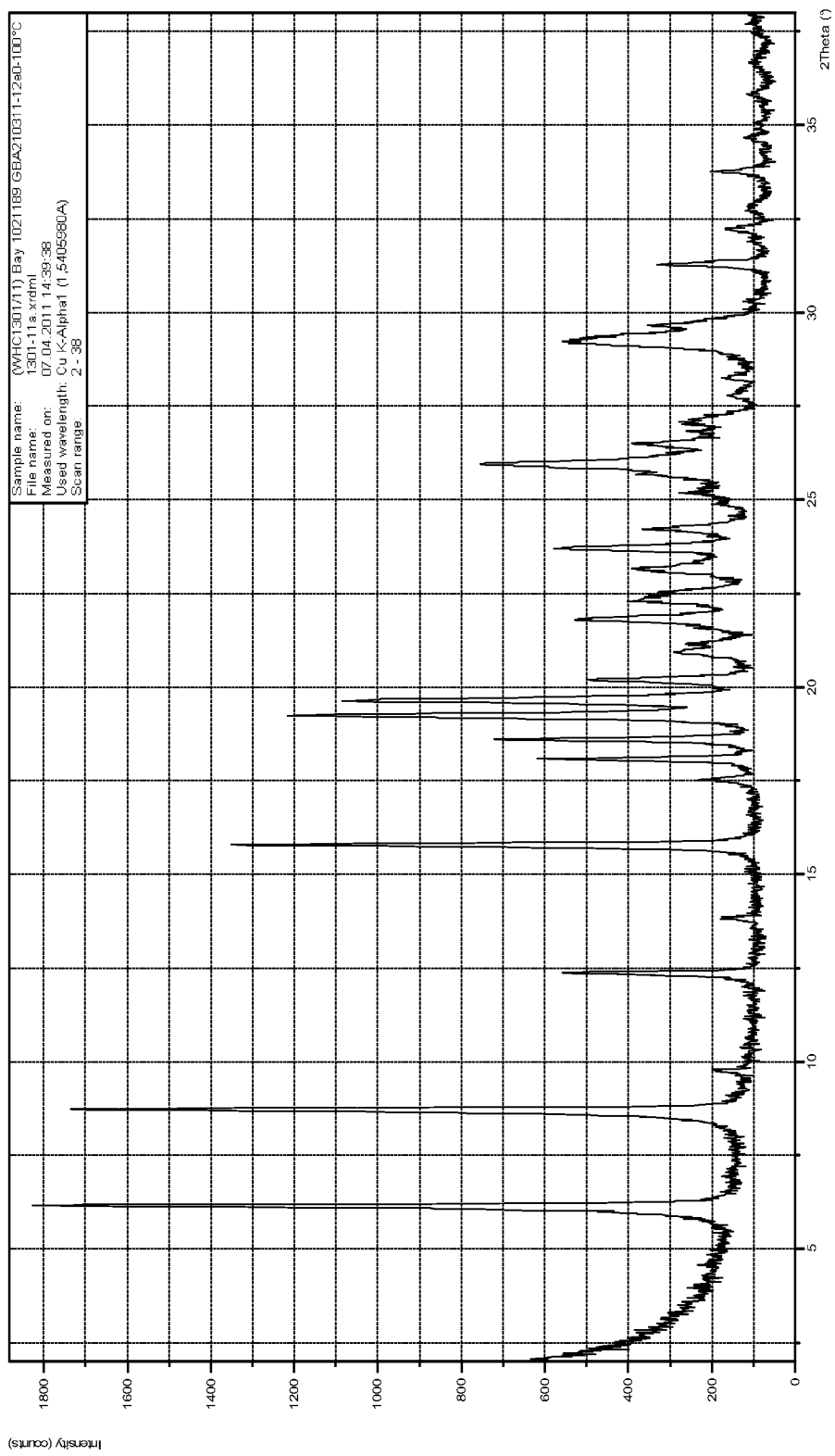
Fig 8: X-ray powder diffractograms of the compound of the formula I in polymorph IV

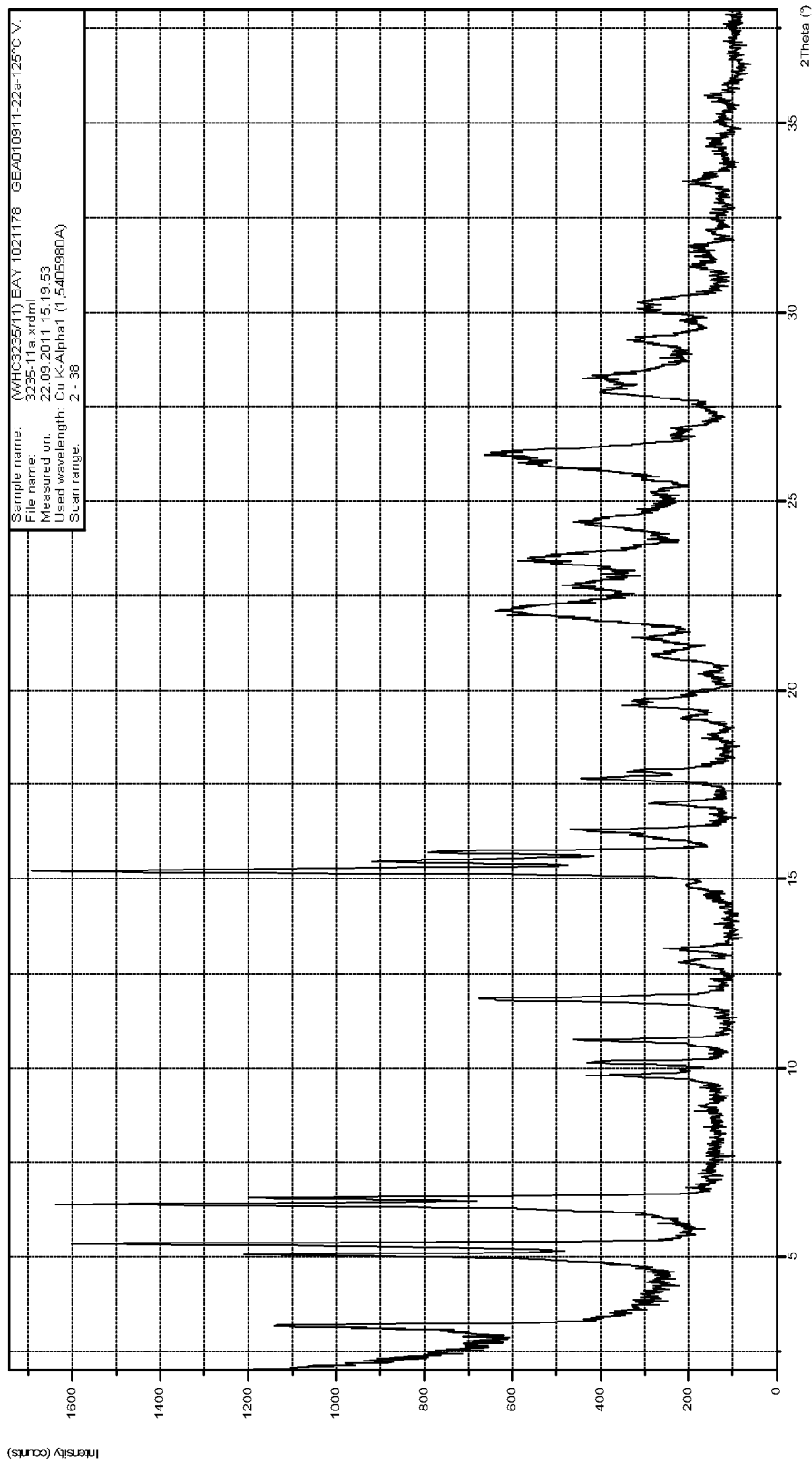
FIG 9: X-ray powder diffractograms of the compound of the formula I in polymorph V

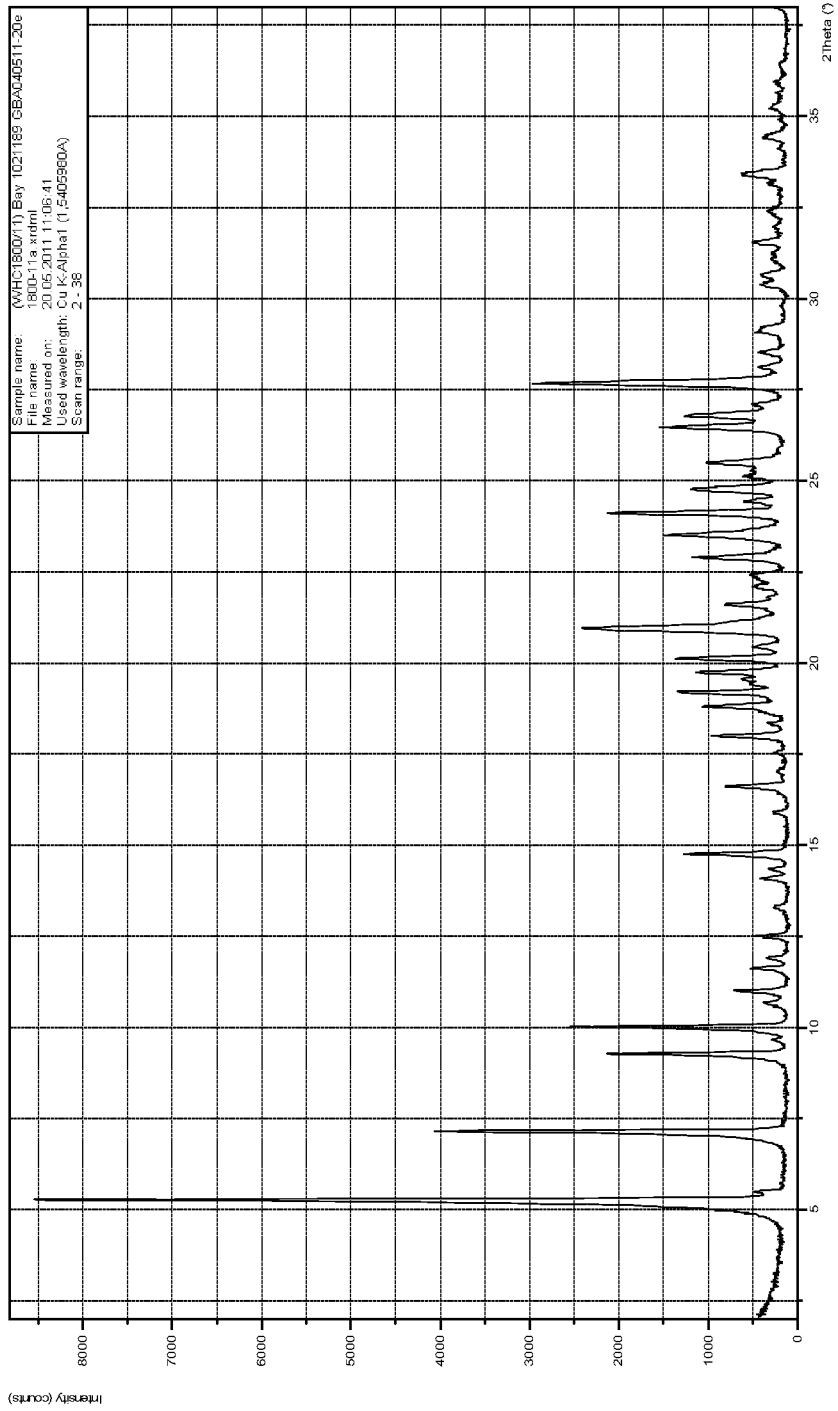
FIG 10: X-ray powder diffractograms of the compound of the formula I as the triacetic acid solvate

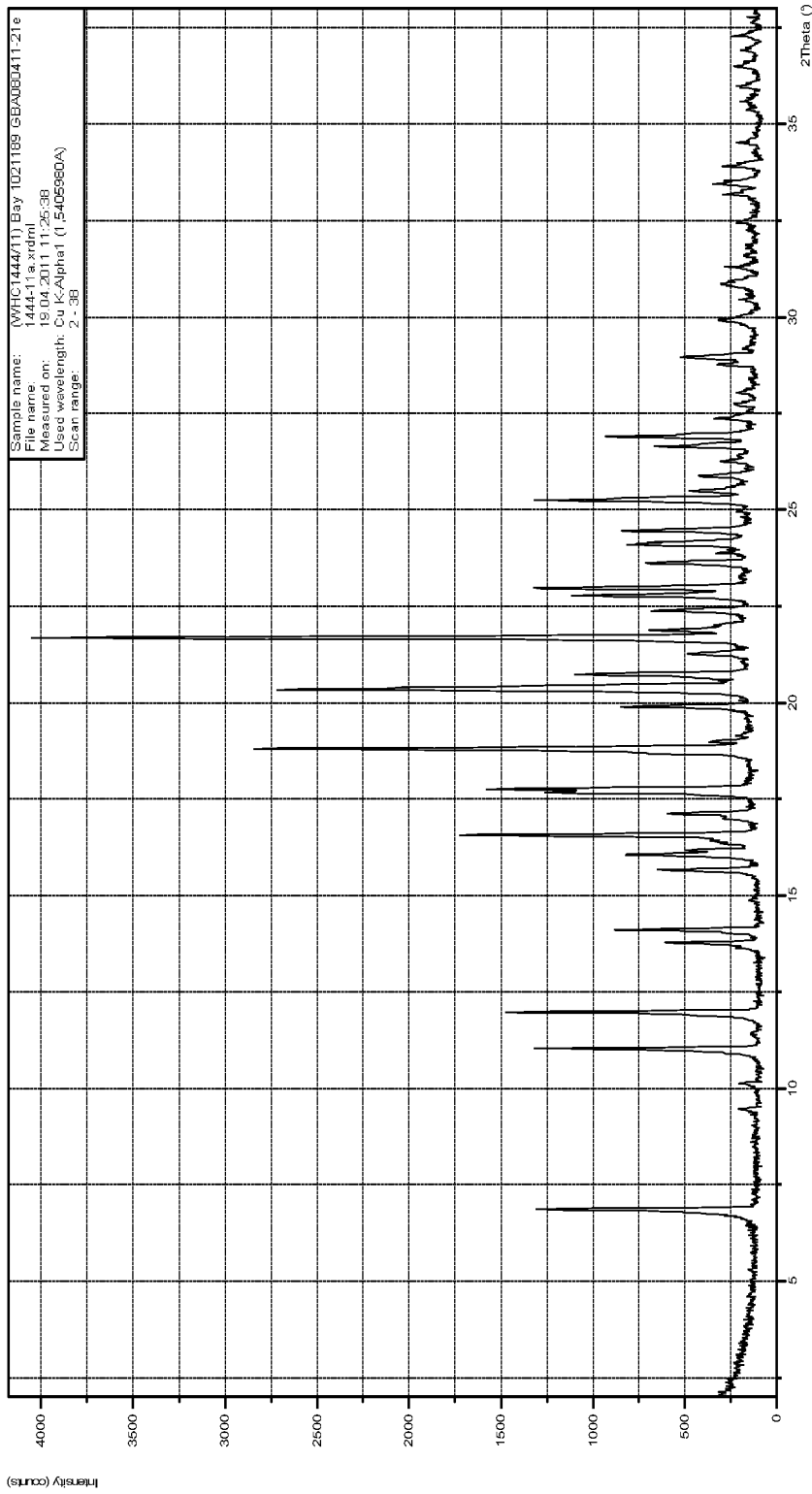
FIG 11: X-ray powder diffractograms of the compound of the formula I as the di-DMSO solvate

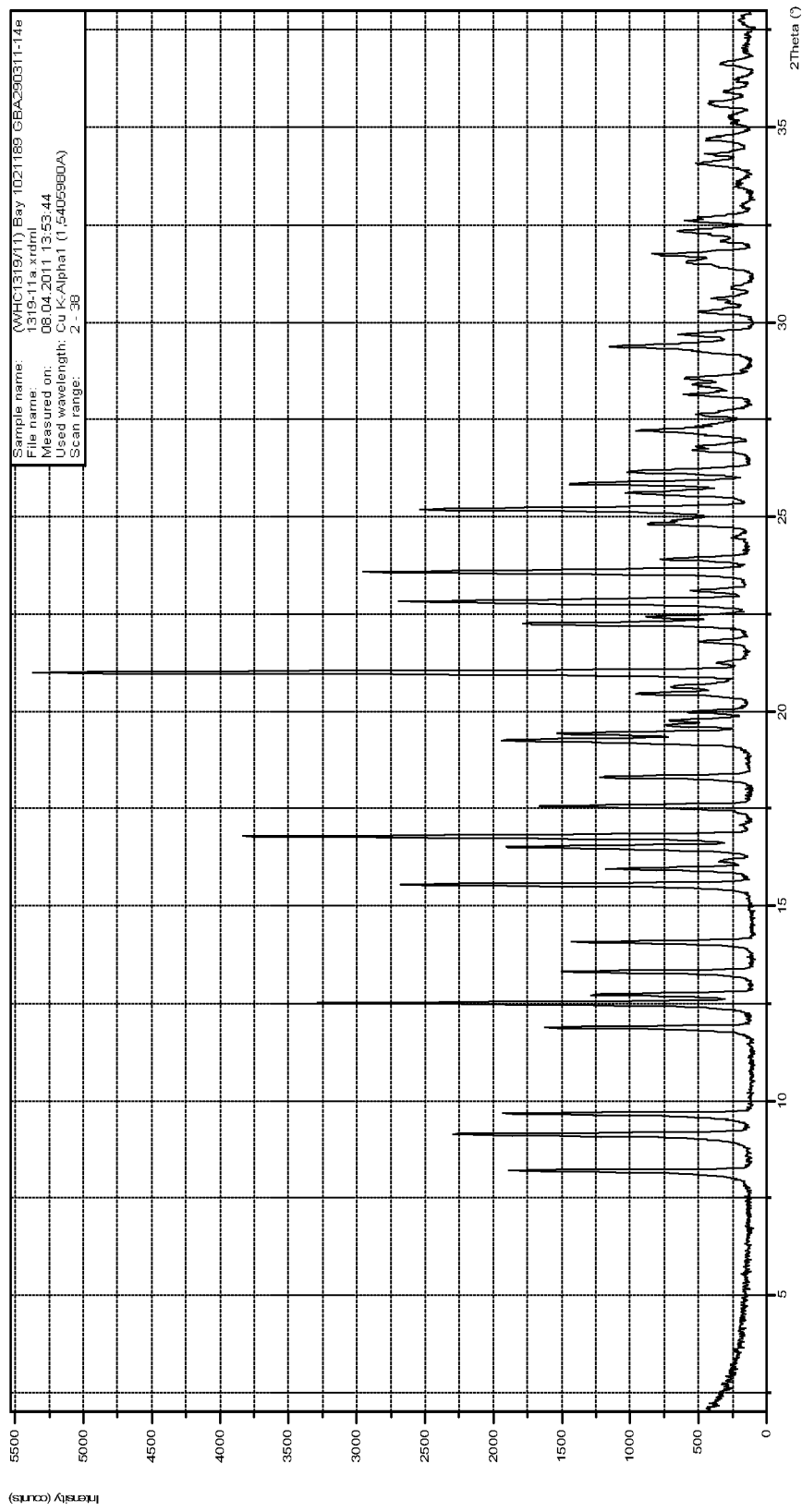
FIG 12: X-ray powder diffractograms of the compound of the formula I as the DMF-water solvate

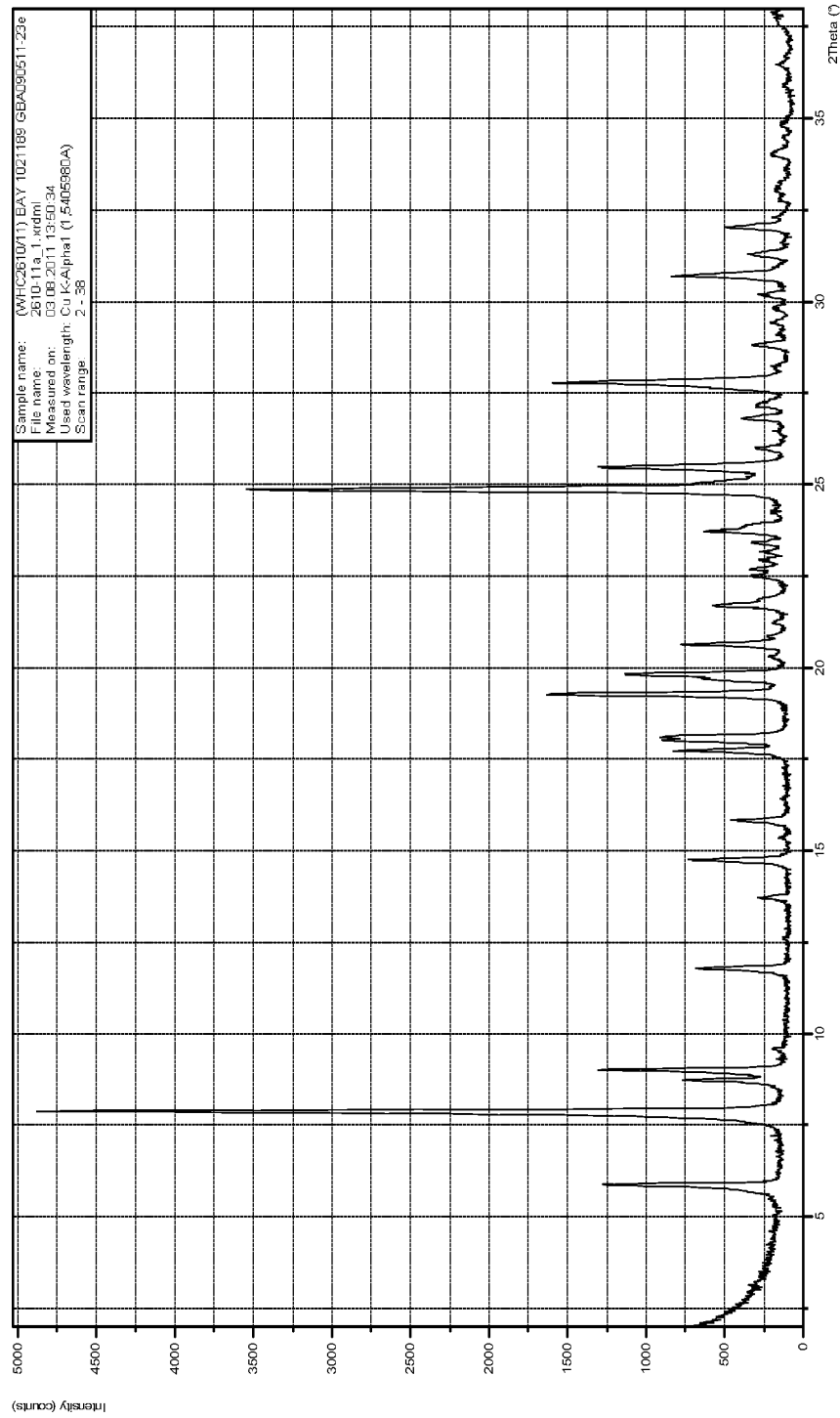
FIG 13: X-ray powder diffractograms of the compound of the formula I as the monohydrate

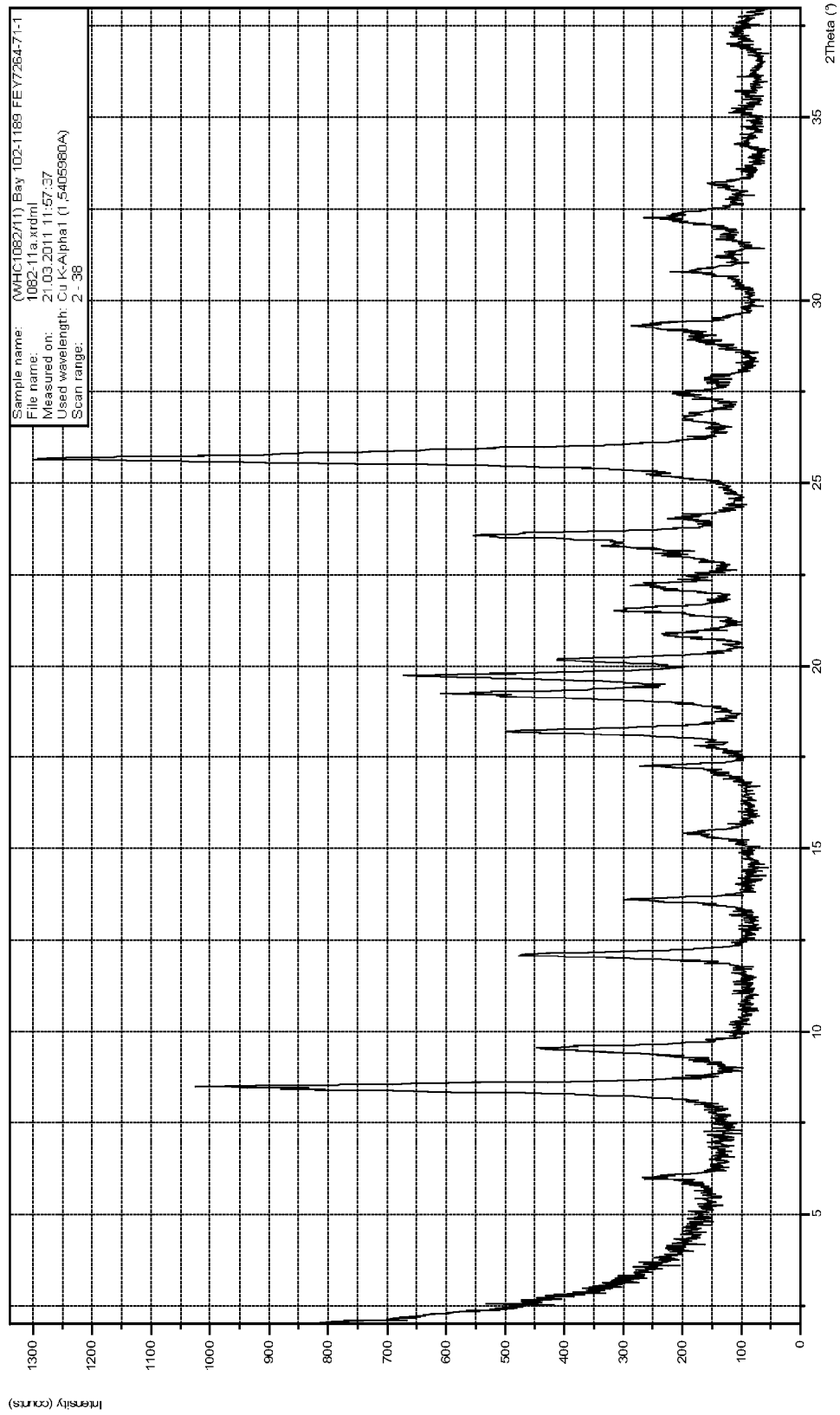
FIG 14: X-ray powder diffractograms of the compound of the formula I as dihydrate

PROCESS FOR PREPARING SUBSTITUTED 5-FLUORO-1H-PYRAZOLOPYRIDINES

The present application relates to a novel and efficient process for preparing novel substituted 5-fluoro-1H-pyrazolopyridines of the formula (VI)

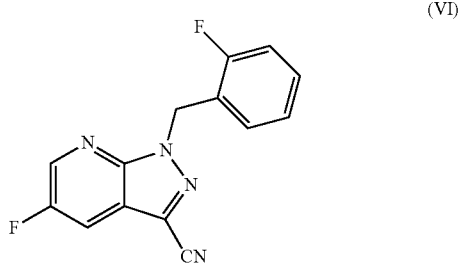 [SMILES: N#Cc1nn(Cc2ccccc2F)c2ncc(F)cc12]

(VI)

which serve as an intermediate for production of medicaments and for production of medicaments for treatment and/or prophylaxis of cardiovascular disorders.

More particularly, the 5-fluoro-1H-pyrazolopyridines of the formula (VI) are suitable for preparation of compound of the formula (I)

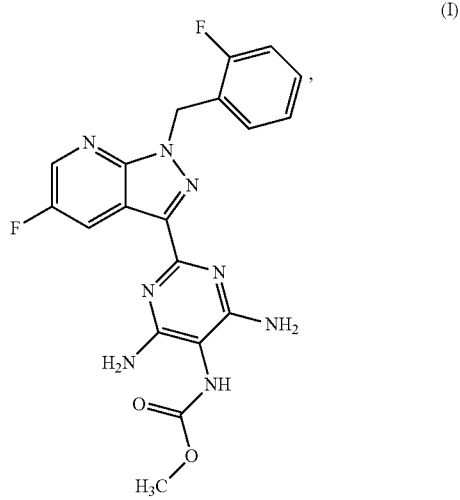 [SMILES: COC(=O)Nc1c(N)nc(-c2nn(Cc3ccccc3F)c3ncc(F)cc23)nc1N]

(I)

which serves for production of medicaments and for production of medicaments for treatment and/or prophylaxis of cardiovascular disorders.

The compound of the formula (I) acts as a stimulator of soluble guanylate cyclase and can be used as an agent for prophylaxis and/or treatment of cardiovascular disorders, for example for treatment of hypertension and heart failure, stable and unstable angina pectoris, peripheral and cardiac vascular disorders, of arrthythmias, for treatment of thromboembolic disorders and ischaemias such as myocardial infarction, stroke, transitory and ischaemic attacks, peripheral perfusion disorders, prevention of restenoses such as after thrombosis therapy, percutaneous transluminal angioplasty (PTA), percutaneous transluminal coronary angioplasty (PTCA), bypass, and for treatment of arteriosclerosis, asthmatic disorders and diseases of the urogenital system, for example prostate hypertrophy, erectile dysfunction, female sexual dysfunction, osteoporosis, glaucoma, pulmonary hypertension, gastroparesis, scleroderma and incontinence.

The compound of the formula (I) may be present in various crystal forms and solvates. The compound of the formula (I) exists in five polymorphs with melting points 257° C. (polymorph I), 253° C. (polymorph II), 247° C. (polymorph III), 246° C. (polymorph IV), 234° C. (polymorph V), a dimethylformamide/water solvate (DMF content 13.6%, water content 0.9%), a di-dimethyl sulphoxide solvate (stoichiometric value: 26.8% DMSO), a triacetic acid solvate (29.7% acetate), a monohydrate (4.1% water) and a dihydrate (7.8% water). The prior art, WO 2011/147809, describes the compound of the formula (I) in Example 1 as a substance.

The crystal polymorph of the compound of the formula (I) in polymorph (I) is notable for stability and particularly for the fact that it is stable even in the micronization process and thus no conversion and recrystallization takes place.

The di-dimethyl sulphoxide solvate of the compound of the formula (I) has the advantage of much better filterability than the substance in the prior art. Furthermore, the preparation process via the di-dimethyl sulphoxide solvate of the compound of the formula (I) leads to a very high purity of the compound of the formula (I).

WO 03/095451, WO 2011/064156 and WO 2011/064171 disclose the synthesis of pyrazolopyridines unsubstituted on the pyridine ring. In these disclosures, the bicyclic ring system is built up by reaction of phenylbenzyl hydrazine with ethyl cyanopyruvate. This synthesis method is unsuitable for the formation of 5-fluoro-1H-pyrazolopyridines.

WO 2009/018415 describes the synthesis of 5-fluoro-1H-pyrazolo[3,4-b]pyridine-3-amine E. Selective dechlorination of the nicotinic acid A to give the compound B, subsequent conversion to the amide C, the reduction thereof to the nitrile and the final cyclization with hydrazine hydrate form the 5-fluoro-1H-pyrazolo[3,4-b]pyridine core. Scheme 1 below illustrates the synthesis.

Scheme 1:

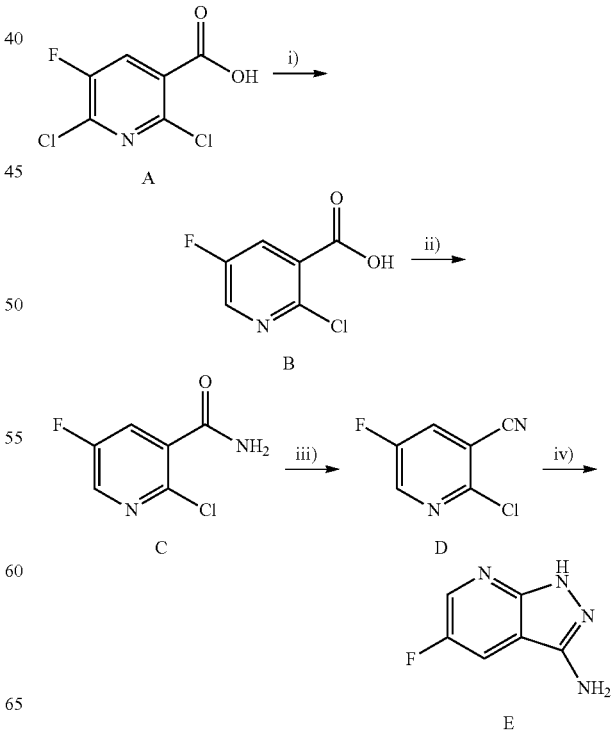

[i) Pd(OAc)₂, PPh₃, NEt₃, HCO₂H; ii) 1) (COCl)₂, CH₂Cl₂, cat. DMF, 2) NH₃ (g), dioxane, iii) TFAA, NEt₃; iv) H₂NNH₂x H₂O, n-BuOH].

A disadvantage of this process is that, proceeding from 5-fluoro-1H-pyrazolo[3,4-b]pyridine E, further steps such as the diazotization reaction and conversion to the iodo compound, followed by an alkylation with a benzyl derivative and subsequent functionalization for introduction of the cyano group are required in order to obtain the desired 5-fluoro-1H-pyrazolopyridines of the formula (VI). This is illustrated by way of example in Scheme 2.

Scheme 2:

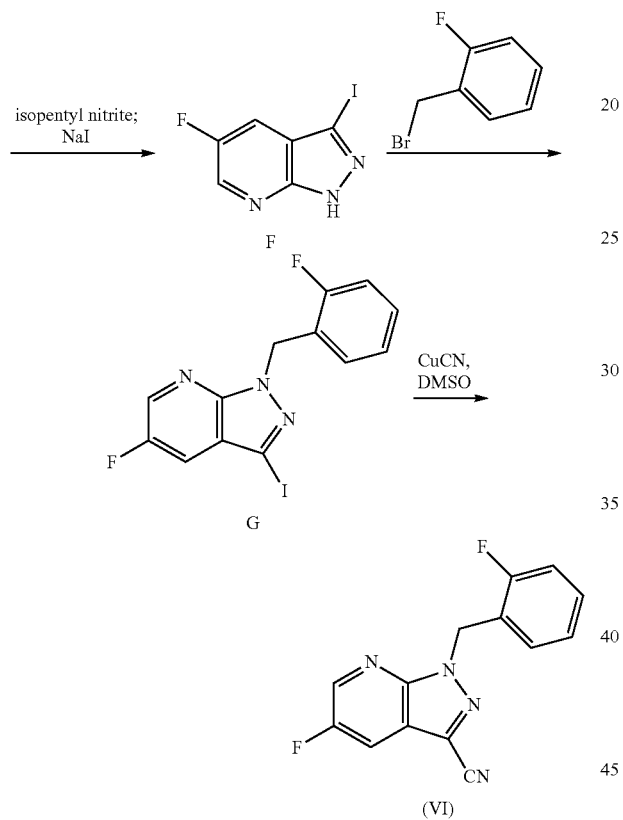

A further disadvantage is that the diazotization is conducted under anhydrous conditions and the diazonium salt has to be isolated, which necessitates considerable safety precautions on conversion to the industrial scale and thus causes high production costs.

A further disadvantage is that the alkylation with a benzyl derivative proceeds unselectively and the product is obtained in only a low yield after complex purification and separation of the isomers.

A further disadvantage is that, in the course of cyanation, toxic copper cyanide has to be handled, which necessitates additional safety precautions in the preparation and in the disposal of mother liquors and aqueous phases, and thus causes high production costs.

A further disadvantage is that the preparation of 5-fluoro-1H-pyrazolopyridines of the formula (VI), according to the process described in Scheme 1, entails the preparation and purification of seven intermediates and affords only a small overall yield.

It is an object of the present invention to provide an efficient process with high yield for preparation of 5-fluoro-1H-pyrazolopyridines of the formula (VI)

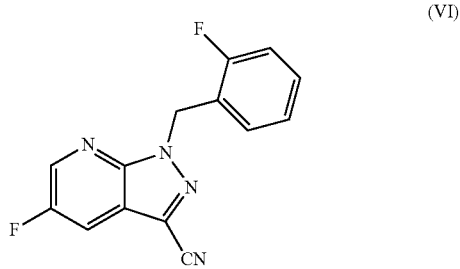 [SMILES: N#Cc1nn(Cc2ccccc2F)c2ncc(F)cc12]

as a key component for an efficient process with high yield for preparation of compound of the formula (I)

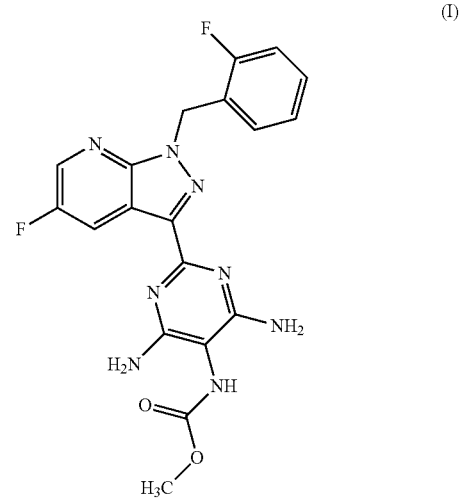 [SMILES: COC(=O)Nc1c(N)nc(-c2nn(Cc3ccccc3F)c3ncc(F)cc23)nc1N]

and the N-oxides, salts, solvates, salts of N-oxides and solvates of the N-oxides and salts thereof.

This object is achieved in accordance with the present invention, as follows. Scheme 3 below illustrates the individual reaction steps by way of example.

Scheme 3:

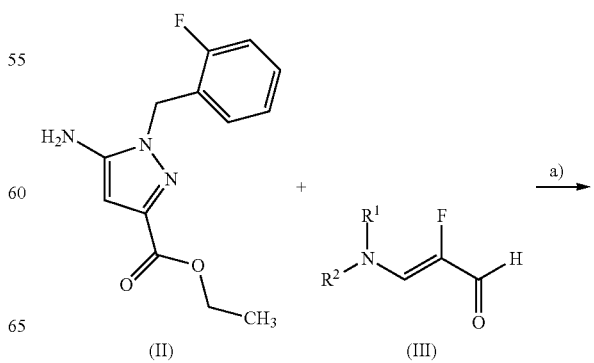

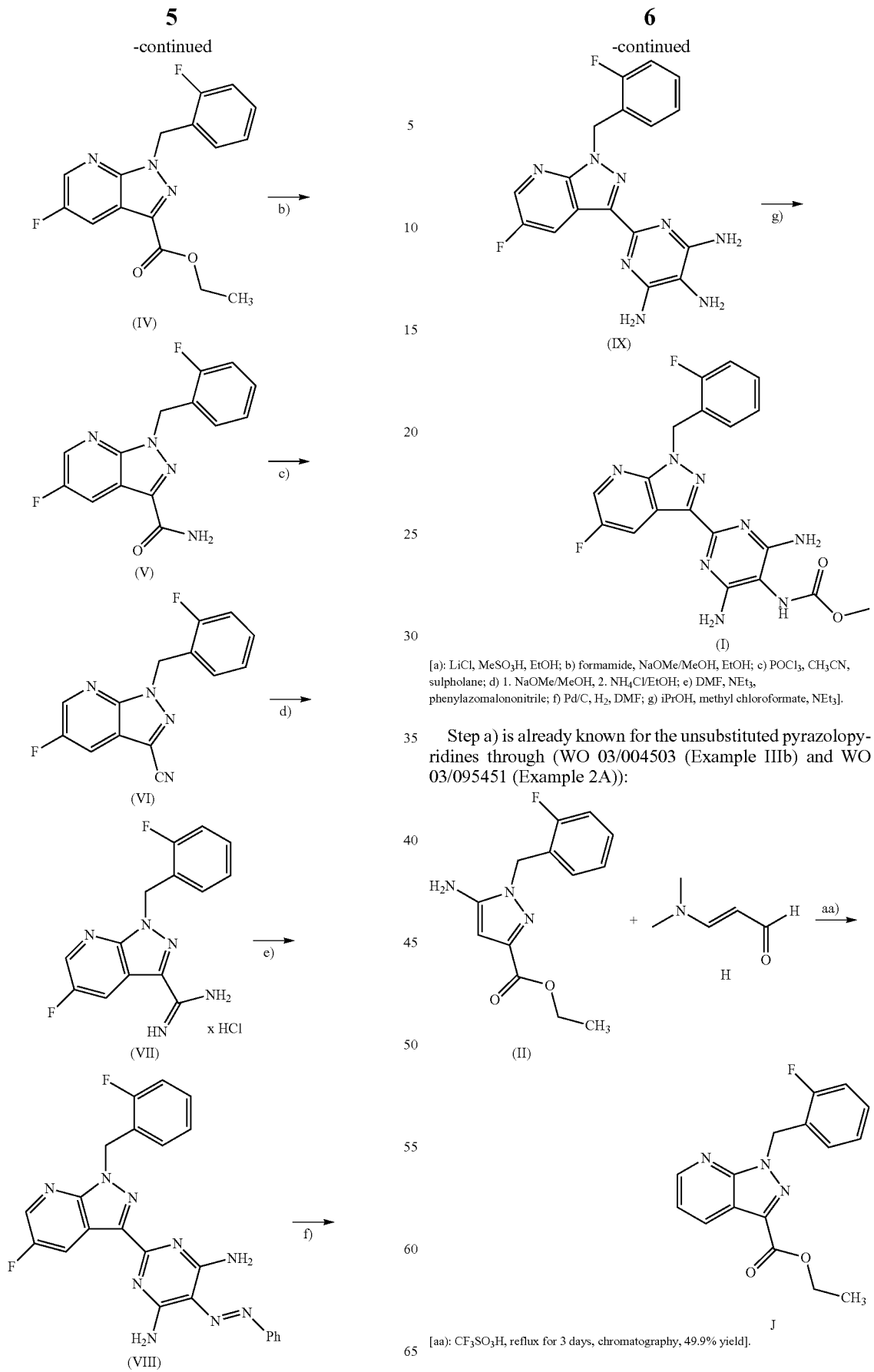
[a]: LiCl, MeSO₃H, EtOH; b) formamide, NaOMe/MeOH, EtOH; c) POCl₃, CH₃CN, sulpholane; d) 1. NaOMe/MeOH, 2. NH₄Cl/EtOH; e) DMF, NEt₃, phenylazomalononitrile; f) Pd/C, H₂, DMF; g) iPrOH, methyl chloroformate, NEt₃].
Step a) is already known for the unsubstituted pyrazolopyridines through (WO 03/004503 (Example IIIb) and WO 03/095451 (Example 2A)):
[aa): CF₃SO₃H, reflux for 3 days, chromatography, 49.9% yield].

Compared to the prior art (WO 03/004503, Example IIIb and WO 03/095451, Example 2A), the preparation of IV proceeds with a much higher yield.

A further advantage is that, rather than the corrosive trifluoroacetic acid, ethanol, which is much less expensive, is used as the solvent.

A further advantage is that the reaction time is considerably shorter compared to the prior art.

A further advantage is that the preparation of IV proceeds with high selectivity and the product is formed in high purity without significant by-product formation, and no complex purification procedures are required.

A further advantage is that IV is obtained by crystallization in high yield and purity.

Steps d)-g) are already known for the unsubstituted pyrazolopyridines through WO 03/095451, WO 2011/064156 and WO 2011/064171 and can be used analogously.

Specifically, the process according to the invention for preparing a compound of the formula (VI)

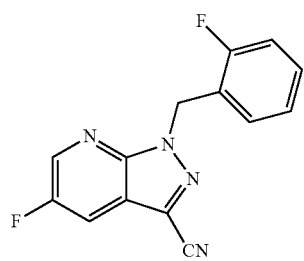

(VI)

comprises the cyclization of the 5-aminopyrazole derivative (IIa)

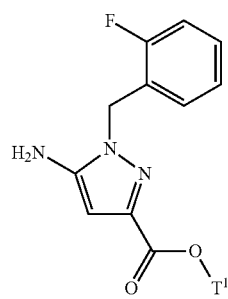

(IIa)

in which
T¹ is (C1-C4)-alkyl,
in the presence of a suitable acid with the aldehyde (III)

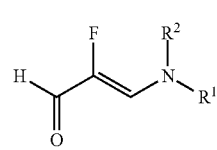

(III)

in which R¹ and R² are each independently methyl, ethyl, isopropyl, phenyl or, together with the nitrogen atom to which they are bonded, are

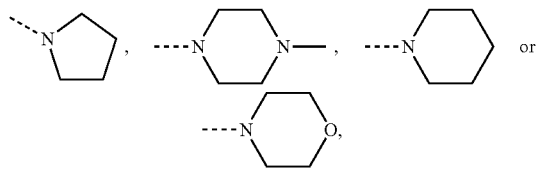

to give the ester of the formula (IVa)

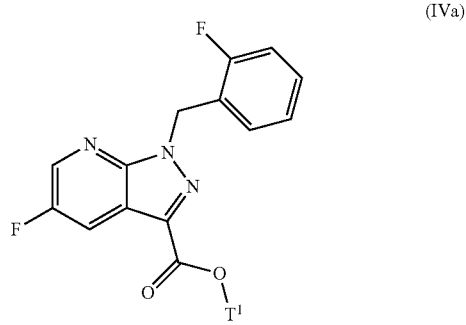

(IVa)

in which T¹ is as defined above, the subsequent reaction thereof with ammonia or formamide to give the amide of the formula (V)

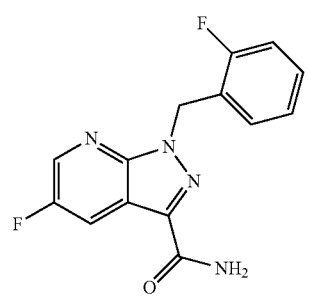

(V)

and the subsequent dehydration to give the nitrile (VI).

The present invention further provides for the use of the compound of the formula (VI)

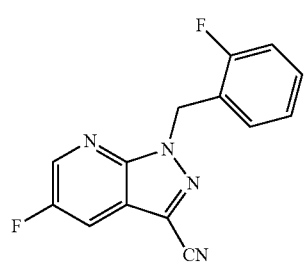

(VI)

for preparation of the compound of the formula (I)

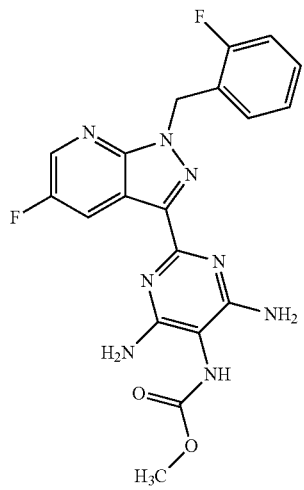
(I)

and the N-oxides, salts, solvates, salts of N-oxides and solvates of the N-oxides and salts thereof.

The present invention further provides for the use of the compound of the formula (III)

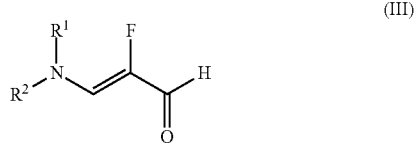
(III)

in which R¹ and R² are each independently methyl, ethyl, isopropyl, phenyl or, together with the nitrogen atom to which they are bonded, are

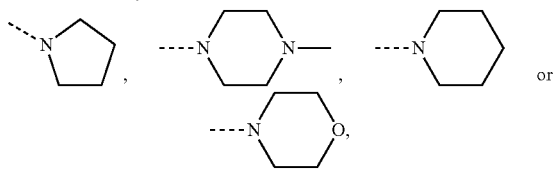
or for preparation of the compound of the formula (I)

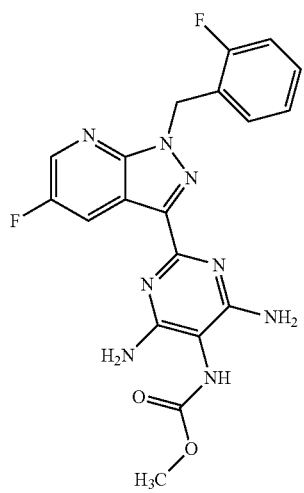
(I)

and the N-oxides, salts, solvates, salts of N-oxides and solvates of the N-oxides and salts thereof.

The present invention further provides for the use of the compound of the formula (VI) for preparation of the compound of the formula (I) as specified above, wherein the compound of the formula (VI) is converted to the compound of the formula (VII)

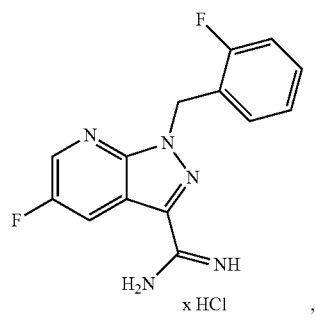
(VII)

the latter is subsequently reacted in an inert solvent in the presence of a suitable base with the compound of the formula (VIIIa)

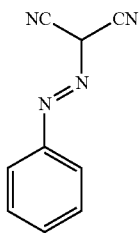
(VIIIa)

to give the compound of the formula (VIII)

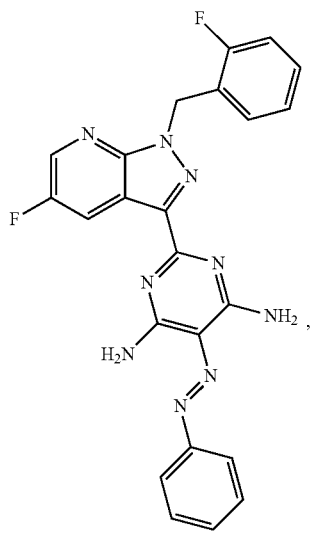
(VIII)

and then the latter is reduced in an inert solvent in the presence of a suitable reducing agent to give the compound (IX)

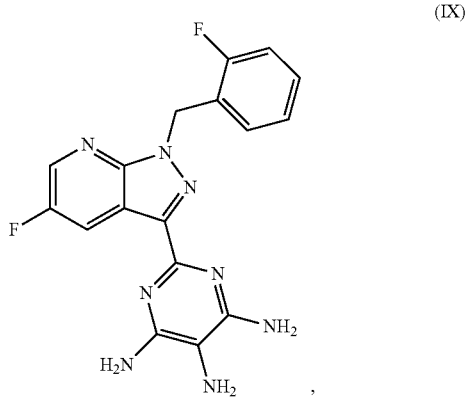 [SMILES: Nc1nc(-c2nn(Cc3ccccc3F)c3ncc(F)cc23)nc(N)c1N]

then the latter is reacted in the presence of a suitable base in the presence or absence of a solvent with methyl chloroformate or with dimethyl dicarbonate to give the compound of the formula (I)

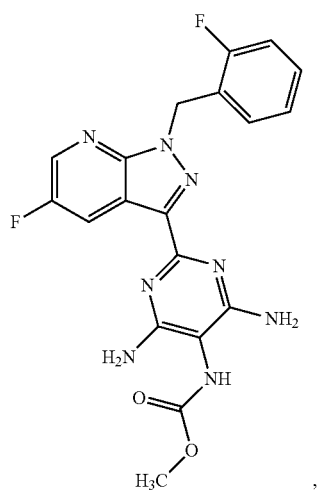

and the resulting compound of the formula (I) is optionally converted with the appropriate (i) solvents and/or (ii) acids or bases to the solvates, salts and/or solvates of the salts thereof.

The conversion (VI)→(VII) is effected by methods known to those skilled in the art in a two-stage process, first to form the imino ester with sodium methoxide in methanol at 0° C. to +40° C. and then nucleophilic addition of one ammonia equivalent, for example ammonia or ammonium chloride, in acetic acid or an alcohol to form the amidine (VII) at +50 to +150° C.

Suitable alcohols for the conversion (VI)→(VII) are alcohols such as methanol, ethanol, n-propanol, isopropanol, n-butanol or tert-butanol.

Inert solvents for the process step (VII)+(VIIIa)→(VIII) are alcohols such as methanol, ethanol, n-propanol, isopropanol, n-butanol or tert-butanol, ethers such as diethyl ether, dioxane, tetrahydrofuran, glycol dimethyl ether or diethylene glycol dimethyl ether, hydrocarbons such as benzene, xylene, toluene, hexane, cyclohexane or mineral oil fractions, or other solvents such as dimethylformamide (DMF), dimethyl sulphoxide (DMSO), sulpholane, N,N'-dimethylpropyleneurea (DMPU), N-methylpyrrolidone (NMP), pyridine, acetonitrile or else water. It is likewise possible to use mixtures of the solvents mentioned. Preference is given to DMF and sulpholane.

Suitable bases for the process step (VII)+(VIIIa)→(VIII) are alkali metal hydroxides, for example lithium hydroxide, sodium hydroxide or potassium hydroxide, alkali metal carbonates such as lithium carbonate, sodium carbonate, potassium carbonate or caesium carbonate, alkali metal hydrogencarbonates such as sodium hydrogencarbonate or potassium hydrogencarbonate, alkali metal alkoxides such as sodium methoxide or potassium methoxide, sodium ethoxide or potassium ethoxide or potassium tert-butoxide, or organic amines such as triethylamine, diisopropylethylamine, pyridine, 1,8-diazabicyclo[5.4.0]undec-7-ene (DBU) or 1,5-diazabicyclo[4.3.0]non-5-ene (DBN). Preference is given to triethylamine.

The reaction (VII)+(VIIIa)→(VIII) is generally conducted within a temperature range of +20° C. to +150° C., preferably at +80° C. to +120° C., optionally in a microwave. The conversion can be effected at standard, elevated or reduced pressure (for example from 0.5 to 5 bar). In general, standard pressure is employed.

The compound of the formula (VIIIa) can be prepared analogously to the literature L. F. Cavalieri, J. F. Tanker, A. Bendich, J. Am. Chem. Soc., 1949, 71, 533.

The reductions (VIII)→(IX) are effected in the presence of a suitable catalyst in an inert solvent within a temperature range of +20° C. to +100° C. under hydrogen pressure (for example from 1 to 100 bar). Preference is given to a temperature range of 40° C. to 80° C. and a hydrogen pressure range of 5 to 70 bar.

Inert solvents for the reduction (VIII)→(IX) are, for example, alcohols such as methanol, ethanol, n-propanol, isopropanol, n-butanol or tert-butanol, ethers such as diethyl ether, dioxane, tetrahydrofuran, glycol dimethyl ether or diethylene glycol dimethyl ether, or other solvents such as dimethylformamide (DMF), dimethyl sulphoxide (DMSO), N,N'-dimethylpropyleneurea (DMPU), N-methylpyrrolidone (NMP), pyridine, acetonitrile or else water. It is likewise possible to use mixtures of the solvents mentioned. Preference is given to DMF and pyridine.

Suitable catalysts for the conversion (VIII)→(IX) are, for example, palladium on activated carbon, platinum on carbon, palladium hydroxide or Raney nickel.

The reduction (VIII)→(IX) can alternatively be effected with a metal or metal salt, for example iron, zinc or tin(II) chloride in a suitable acid, for example hydrogen chloride/hydrochloric acid, sulphuric acid, phosphoric acid or acetic acid, within a temperature range of +20° C. to +140° C.

Inert solvents for process step (IX)→(I) are, for example, alcohols such as methanol, ethanol, n-propanol, isopropanol, n-butanol or tert-butanol, ethers such as diethyl ether, diisopropyl ether, dioxane, tetrahydrofuran, glycol dimethyl ether or diethylene glycol dimethyl ether, halogenated hydrocarbons such as dichloromethane, trichloromethane, carbon tetrachloride, trichloroethylene or chlorobenzene, hydrocarbons such as benzene, xylene, toluene, hexane, cyclohexane or mineral oil fractions, or other solvents such as dimethylformamide (DMF), dimethyl sulphoxide (DMSO), N,N'-dimethylpropyleneurea (DMPU), N-methylpyrrolidone (NMP), acetonitrile, ethyl acetate or else water. It is likewise possible to use mixtures of the solvents mentioned. Preference is given to isopropanol and tetrahydrofuran, and to a mixture of isopropanol and tetrahydrofuran.

Suitable bases for the process step (IX)→(I) are alkali metal hydrides such as sodium hydride, alkali metal hydroxides, for example lithium hydroxide, sodium hydroxide or potassium hydroxide, alkali metal carbonates such as lithium carbonate, sodium carbonate, potassium carbonate or caesium carbonate, alkali metal hydrogencarbonates such as sodium hydrogencarbonate or potassium hydrogencarbonate, alkali metal alkoxides such as sodium methoxide or potassium methoxide, sodium ethoxide or potassium ethoxide or potassium tert-butoxide, or organic amines such as triethylamine, diisopropylethylamine, pyridine, 4-dimethylaminopyridine, 1,8-diazabicyclo[5.4.0]undec-7-ene (DBU) or 1,5-diazabicyclo[4.3.0]non-5-ene (DBN). Preference is given to triethylamine.

The reaction (IX)→(I) is generally conducted within a temperature range of −10° C. to +70° C., preferably at 0° C. to +50° C. The conversion can be effected at standard, elevated or reduced pressure (for example from 0.5 to 5 bar). In general, standard pressure is employed.

Compounds of the formula (IIa) are known from the literature and can be prepared in analogy to Example 20A in WO 00/06569.

Compounds of the formula (III) are known from the literature H. Yamanaka, S. Yamashita and T. Ishihara, Synlett 353-354 (1993). The synthesis disclosed therein is illustrated in Scheme 4.

(10) 1988-1994 (1985), only a yield of 66% is achieved and, in this process, very large amounts (2.79 kg per kg of (XVIb)) of by-product (dimethyldibenzyl nitrobenzenesulphonate) are obtained, which have to be removed and disposed of.

A further disadvantage of this process is that, according to H. Yamanaka, H. Ganbayashi, M. Kuwabara, K. Fukunishi and M. Nomura, Nippon Kagaku Kaishi (7) 1036-1043 (1988), proceeding from (XVIb), the alkylation requires 10 equivalents of the carcinogenic alkylating agent methyl iodide.

A further disadvantage of this process is that, according to H. Yamanaka, S. Yamashita and T. Ishihara, Synlett 353-354 (1993), the reaction of O with morpholine forms not only the desired product (IIIb) but also 11% of the by-product (IIIa), which necessitates a complex purification, the result being that the overall synthesis for preparation of (IIIb) gives only a low overall yield and causes high production costs.

The synthesis described therein, however, is unsuitable for the preparation of the aldehydes of the formula (III) on the industrial scale, and so a new and efficient synthesis has been developed, which is illustrated by way of example in Scheme 5.

Scheme 5:

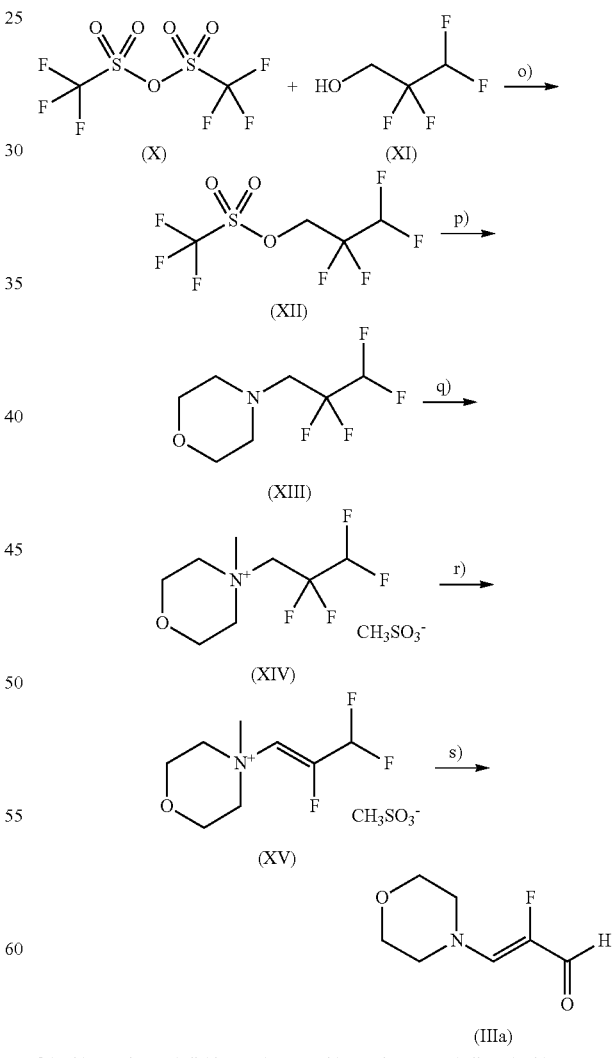

[o) without solvent; p) dichloromethane or without solvent, morpholine; q) without solvent, methyl methanesulphonate; r) NaOH, water; s) morpholine/triethylamine.]

Scheme 4:

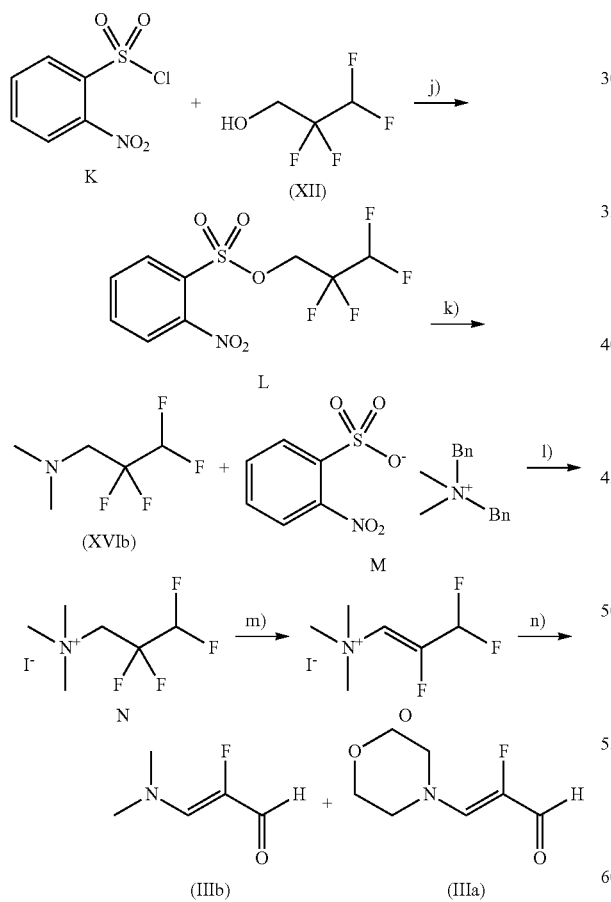

[k) 3 eq dimethylbenzylamine, 130-140° C.; l) 10 eq CH₃I, reflux, m) 1M NaOH, 20° C.; n) DMSO—H₂O (1:1), morpholine, 40° C., 3 h].

A disadvantage of this process is that, in the preparation of (XVIb), according to H. Yamanaka, M. Kuwabara, M. Okudo, K. Fukunishi and M. Nomura, Nippon Kagaku Kaishi The compound of the formula (XIII) is known according to the literature Markovskii, L. N.; Kolesnik, N. P.; Shermolovich, Yu. G Zhurnal Obshchei Khimii (1980), 50(4), 826-829. The synthesis disclosed therein is illustrated in Scheme 6.

Scheme 6:

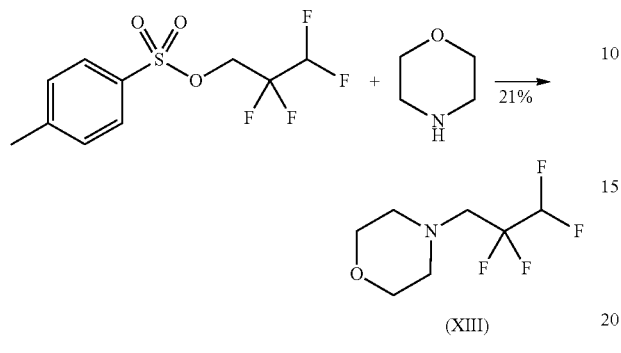

(XIII)

The synthesis described therein, however, for reasons including the low yield, is unsuitable for the preparation of the aldehydes of the formula (III) on the industrial scale.

The present invention further provides a process for preparing compounds of the formula (III)

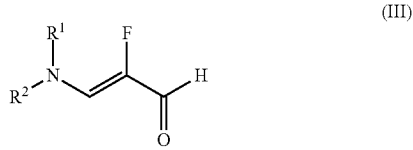

(III)

in which $R^1$ and $R^2$ are each independently methyl, ethyl, isopropyl, phenyl or, together with the nitrogen atom to which they are bonded, are

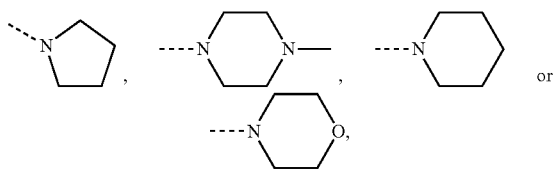

wherein trifluoromethanesulphonic anhydride of the formula (X) is reacted with 2,2,3,3-tetrafluoro-1-propanol of the formula (XI) without solvent and the resulting 2,2,3,3-tetrafluoropropyl trifluoromethanesulphonate of the formula (XII) is reacted with a compound of the formula (XIIa)

(XIIa)

in which $R^1$ and $R^2$ are each as defined above to give a compound of the formula (XIIIa)

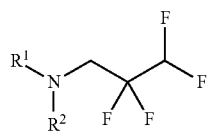

(XIIIa)

in which $R^1$ and $R^2$ are each as defined above
and with methyl methanesulphonate to give a compound of the formula (XIVa)

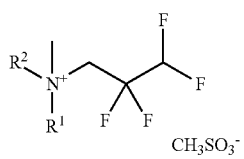

(XIVa)

in which $R^1$ and $R^2$ are each as defined above
and with sodium hydroxide to give a compound of the formula (XVa)

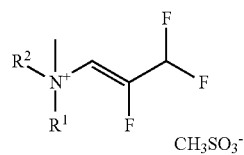

(XVa)

in which $R^1$ and $R^2$ are each as defined above
and finally converted under basic conditions to give the compound of the formula (III).

The present invention further preferentially provides a process for preparing compounds of the formula (IIIa)

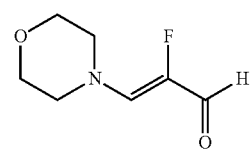

(IIIa)

wherein trifluoromethanesulphonic anhydride of the formula (X) is reacted with 2,2,3,3-tetrafluoro-1-propanol of the formula (XI) without solvent and the resulting 2,2,3,3-tetrafluoropropyl trifluoromethanesulphonate of the formula (XII) is reacted with morpholine to give a compound of the formula (XIII)

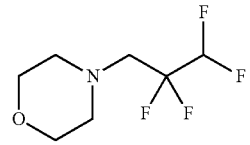

(XIII)

and with methyl methanesulphonate to give a compound of the formula (XIV)

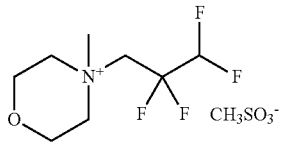
(XIV)

and with sodium hydroxide to give a compound of the formula (XV)

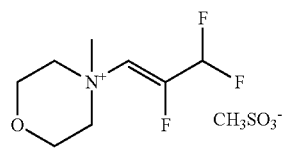
(XV)

and finally with addition of morpholine to give the compound of the formula (III).

The new synthesis has the advantage over the prior art that the intermediate (XII) and the intermediates (XIV) and (XV) unknown to date need not be isolated, which greatly reduces the industrial complexity of the synthesis.

The yields of the resulting aldehydes of the formula (III) are much higher with the new synthesis process than in the prior art.

"Basic conditions" in the context of the invention for the process step (XIVa) to (XVa) means that the acid formed in the reaction is scavenged by auxiliary bases, for example sodium hydroxide, potassium hydroxide, potassium carbonate, sodium carbonate, or triethylamine to form the corresponding salts.

Compared to the prior art, the preparation of (XIII) proceeds with a much higher yield. It is advantageous that no solvent is required for preparation of (XII), and that the intermediate XII is used without further purification in the subsequent stage to give (XIII).

A further advantage of this process is that no significant wastes are formed in the preparation of (XIII). It is also advantageous that the trifluoromethanesulphonic acid and morpholine can be recovered from the morpholinium trifluoromethanesulphonate formed.

Compared to the prior art, the preparation of (XIV) requires only one equivalent of the alkylating agent. The reaction is conducted without solvent and proceeds virtually quantitatively, which achieves a high space-time yield.

A further advantage of this process is that the product (XIV) is not isolated, (XIV) is dissolved in water and this solution is reacted with sodium hydroxide solution to give (XV).

A further advantage of this process is that the product (XV) is also not isolated; reaction of the aqueous solution with morpholine affords (IIIa) as the sole product in high yield.

A further advantage of this process is that (IIIa) is obtained in high overall yield and purity by crystallization.

The cyclization of the 5-aminopyrazole derivative of the compound (IIa) with the aldehyde of the compound (III) to give the compound of the formula (IV) is effected in an inert solvent, optionally in the presence of an acid and optionally of an alkali metal salt, within a temperature range of +10° C. to +200° C., preferably at +20° C. to +100° C., at standard pressure, within, for example 2 to 50 hours, preferably within 2 to 20 hours.

Acids are, for example, hydrochloric acid, trifluoroacetic acid and methanesulphonic acid. Preference is given to methanesulphonic acid and hydrochloric acid.

Alkali metal salts are sodium chloride or lithium chloride. A preferred alkali metal salt is lithium chloride.

Inert solvents are, for example, alcohols such as methanol, ethanol, n-propanol or isopropanol, n-butanol, ethers such as diethyl ether, dioxane, tetrahydrofuran, glycol dimethyl ether or diethylene glycol dimethyl ether, hydrocarbons such as benzene, toluene, xylene, hexane, cyclohexane or mineral oil fractions or other solvents, acetonitrile or N,N-dimethylformamide, or mixtures of solvents. Preference is given to ethanol, diethylene glycol dimethyl ether or dioxane.

The preferred formation of the amide (IVa)→(V) is effected by reaction in an inert solvent with formamide in the presence of a base within a temperature range of 0° C. to +150° C., preferably of +20° C. to +130° C., at standard pressure or elevated pressure, within 2 to 24 hours.

Inert solvents are, for example, alcohols such as methanol, ethanol, n-propanol or iso-propanol. Preference is given to ethanol.

Suitable bases for the preferred process step (IVa)→(V) are alkali metal carbonates such as lithium carbonate, sodium carbonate, potassium carbonate or caesium carbonate, alkali metal hydrogencarbonates such as sodium hydrogencarbonate or potassium hydrogencarbonate, alkali metal alkoxides such as sodium methoxide or potassium methoxide, sodium ethoxide or potassium ethoxide or potassium tert-butoxide, or organic amines such as triethylamine, diisopropylethylamine, pyridine, 1,8-diazabicyclo[5.4.0]undec-7-ene (DBU) or 1,5-diazabicyclo[4.3.0]non-5-ene (DBN). Preference is given to sodium methoxide and sodium ethoxide.

The formation of the amide (IVa)→(V) is alternatively effected by reaction with ammonia within a temperature range of 0° C. to +50° C., preferably of +20° C. to +30° C., at standard pressure or elevated pressure, within 24 to 72 hours.

Inert solvents are, for example, alcohols such as methanol, ethanol, n-propanol or isopropanol. Preference is given to using a solution of ammonia in methanol in a concentration of 5N to 7N.

The dehydration of the amide (V) to the nitrile (VI) is effected in an inert solvent, optionally in the presence of a suitable base, with a suitable dehydrating agent, for example phosphorus oxychloride, trifluoroacetic anhydride, acetic anhydride or trifluoromethanesulphonic anhydride, within a temperature range of 0° C. to +150° C., preferably at +50° C. to +110° C., within 1 to 12 hours.

Preference is given to phosphorus oxychloride.

Inert solvents are ethers such as diethyl ether, dioxane, tetrahydrofuran (THF), glycol dimethyl ether or diethylene glycol dimethyl ether, hydrocarbons such as benzene, toluene, xylene, hexane, cyclohexane or mineral oil fractions or other solvents, pyridine, sulpholane, acetonitrile or N,N-dimethylformamide, or mixtures of solvents. Preference is given to sulpholane and acetonitrile.

Suitable bases are, for example, organic amines such as triethylamine, diisopropylethylamine, pyridine, 1,8-diazabicyclo[5.4.0]undec-7-ene (DBU) or 1,5-diazabicyclo[4.3.0]non-5-ene (DBN). Preference is given to pyridine.

The compounds described in the context of the process according to the invention may also be in the form of the salts, solvates or solvates of the salts thereof.

The compounds described in the context of the process according to the invention may, depending on the structure, also be in the form of the tautomers thereof.

Preferred salts in the context of the invention are physiologically acceptable salts of the compounds used and prepared in the process according to the invention.

Physiologically acceptable salts of the compounds used and prepared in the process according to the invention include acid addition salts of mineral acids, carboxylic acids and sulphonic acids, for example salts of hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, propionic acid, lactic acid, tartaric acid, malic acid, citric acid, fumaric acid, maleic acid and benzoic acid.

Physiologically acceptable salts of the compounds used and prepared in the process according to the invention also include salts of customary bases, by way of example and with preference alkali metal salts (e.g. sodium and potassium salts), alkaline earth metal salts (e.g. calcium and magnesium salts) and ammonium salts derived from ammonia or organic amines having 1 to 16 carbon atoms, by way of example and with preference ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, dihydroabiethylamine, arginine, lysine, ethylenediamine and methylpiperidine.

In the context of the invention, solvates refer to those forms of the compounds used and prepared in the process according to the invention which, in the solid or liquid state, form a complex by coordination with solvent molecules. Hydrates are a specific form of the solvates in which the coordination is with water.

In the context of the present invention, the substituents, unless specified otherwise, are each defined as follows:

Alkyl in the context of the invention is a linear or branched alkyl radical having 1 to 4 carbon atoms. Preferred examples include: methyl, ethyl, n-propyl, isopropyl, n-butyl, iso-butyl, sec-butyl and tert-butyl.

The present invention is illustrated in detail below by non-limiting preferred examples and comparative examples. Unless stated otherwise, all amounts given refer to percentages by weight.

The present invention provides a process for preparing compounds of the formula (VI)

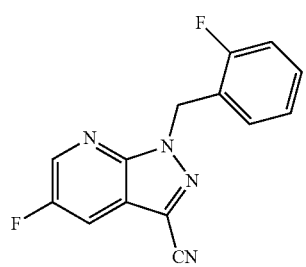

characterized in that the compound of the formula (V)

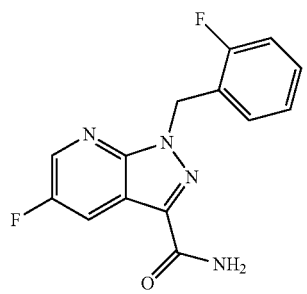

is prepared by reaction of an ester of the formula (IVa)

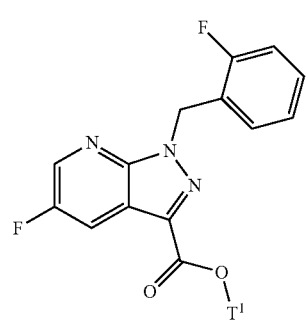

in which
$T^1$ is (C1-C4)-alkyl
with formamide.

The present invention further provides a process as described above, characterized in that an ester of the formula (IVa) is prepared by cyclization of the 5-aminopyrazole derivative (IIa)

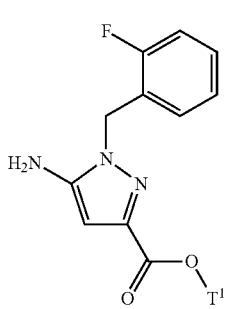

in which
$T^1$ is (C1-C4)-alkyl
in the presence of an acid and an alkali metal salt with an aldehyde of the formula (III)

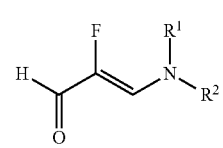

in which $R^1$ and $R^2$ are each independently methyl, ethyl, isopropyl, phenyl or, together with the nitrogen atom to which they are bonded, are

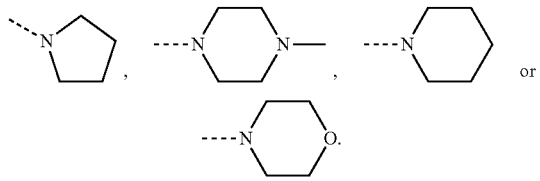

The present invention further provides a process as described above, characterized in that the aldehyde used in the cyclization reaction is the compound of the formula (IIIa)

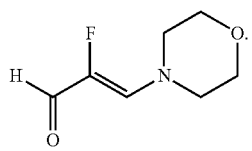

(IIIa)

The present invention further provides a process for preparing aldehydes of the formula (III)

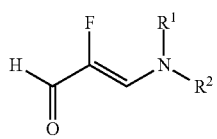

(III)

in which $R^1$ and $R^2$ are each independently methyl, ethyl, isopropyl, phenyl or, together with the nitrogen atom to which they are bonded, are

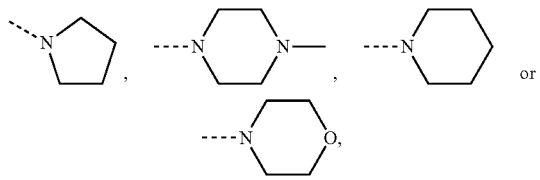

characterized in that trifluoromethanesulphonic anhydride is reacted with 2,2,3,3-tetrafluoro-1-propanol without solvent and the resulting 2,2,3,3-tetrafluoropropyl trifluoromethanesulphonate is reacted with a compound of the formula (XIIa)

(XIIa)

in which $R^1$ and $R^2$ are each as defined above, to give a compound of the formula (XIIIa)

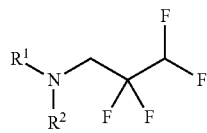

(XIIIa)

in which $R^1$ and $R^2$ are each as defined above
and with methyl methanesulphonate to give a compound of the formula (XIVa)

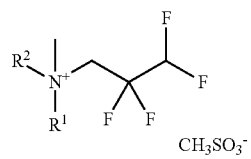

(XIVa)

in which $R^1$ and $R^2$ are each as defined above
and with sodium hydroxide to give a compound of the formula (XVa)

(XVa)

$R^2\!\!\underset{R^1}{\overset{|}{N^+}}\!\!\diagup\!\!\diagdown\!\!\underset{F}{\diagup}\!\!F$    $CH_3SO_3^-$ in which $R^1$ and $R^2$ are each as defined above
and finally converted under basic conditions to give the compound of the formula (III).

The present invention further provides a process for preparing compounds of the formula (IIIa)

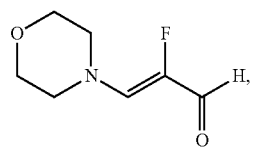

(IIIa)

wherein trifluoromethanesulphonic anhydride of the formula (X) is reacted with 2,2,3,3-tetrafluoro-1-propanol of the formula (XI) without solvent and the resulting 2,2,3,3-tetrafluoropropyl trifluoromethanesulphonate of the formula (XII) is reacted with morpholine to give a compound of the formula (XIII)

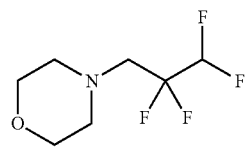

(XIII)

and with methyl methanesulphonate to give a compound of the formula (XIV)

(XIV)

[Chemical structure: N-methylmorpholinium with CF2-CHF2 group, CH3SO3− counterion]

and with sodium hydroxide to give a compound of the formula (XV)

(XV)

[Chemical structure: N-methylmorpholinium vinyl-CHF2, CH3SO3− counterion]

and finally with addition of morpholine to give the compound of the formula (IIIa).

The present invention further provides a process for preparing the compound of the formula (I)

(I)

[Chemical structure of compound (I): 1-(2-fluorobenzyl)-5-fluoro-pyrazolo[3,4-b]pyridine linked to pyrimidine with NH2, H2N, and NH-C(=O)-O-CH3 substituents]

characterized in that compounds of the formula (VI)

(VI)

[Chemical structure of compound (VI): 1-(2-fluorobenzyl)-5-fluoro-3-cyano-pyrazolo[3,4-b]pyridine]

are used, these being characterized in that they are prepared by the process specified above and the resulting compounds of the formula (I) are optionally converted with the appropriate (i) solvents and/or (ii) acids or bases to the solvates, salts and/or solvates of the salts thereof.

The present invention further provides a process for preparing the compound of the formula (I), characterized in that compounds of the formula (VI)

(VI)

[Chemical structure of compound (VI)]

are used, these being characterized in that they are prepared by the processes specified above and the resulting compounds of the formula (I) are optionally converted with the appropriate (i) solvents and/or (ii) acids or bases to the solvates, salts and/or solvates of the salts thereof.

The present invention further provides a process for preparing the compound of the formula (I), characterized in that compounds of the formula (VI)

(VI)

[Chemical structure of compound (VI)]

are used, these being characterized in that they are prepared by the processes specified above and the resulting compounds of the formula (I) are optionally converted with the appropriate (i) solvents and/or (ii) acids or bases to the solvates, salts and/or solvates of the salts thereof.

The present invention further provides a process for preparing compound (I), characterized in that the compound of the formula (VI) is used, this being prepared by the processes specified above, by converting the compound of the formula (VI) to the compound of the formula (VII)

(VII)

[Chemical structure of compound (VII): amidine derivative with H2N-C(=NH)- group, x HCl]

subsequently reacting the latter in an inert solvent in the presence of a suitable base with the compound of the formula (VIIIa)

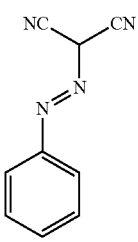

(VIIIa)

to give the compound of the formula (VIII)

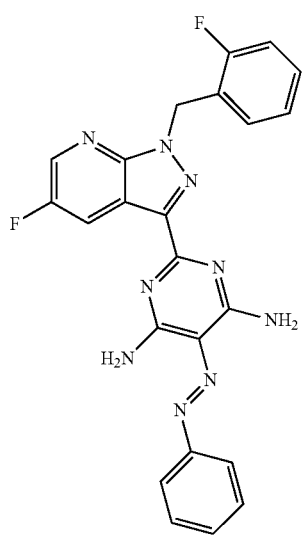

(VIII)

and then reducing the latter in an inert solvent in the presence of a suitable reducing agent to give the compound (IX)

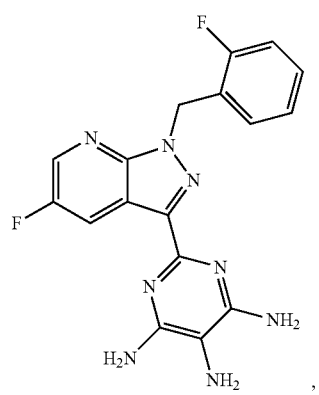

(IX)

and thereafter reacting the latter with methyl chloroformate or with dimethyl dicarbonate in the presence of a suitable base with or without solvent to give the compound of the formula (I), and optionally converting the resulting compounds of the formula (I) with the appropriate (i) solvents and/or (ii) acids or bases to the solvates, salts and/or solvates of the salts thereof.

The present invention further provides the compound of the formula (I) in crystalline form of polymorph I

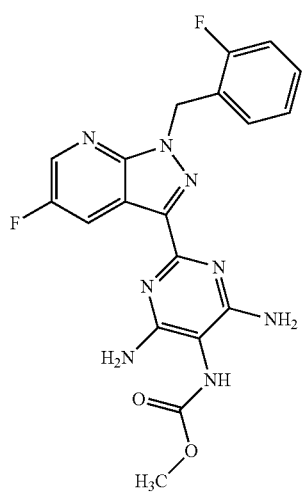

(I)

characterized in that the x-ray diffractogram of the compound exhibits peak maxima of the 2 theta angle at 5.9, 6.9, 22.7.

The present invention further provides the compound of the formula (I) in polymorph (I) as described above, characterized in that the x-ray diffractogram of the compound exhibits peak maxima of the 2 theta angle at 5.9, 6.9, 16.2, 16.5, 24.1, 22.7, 24.7.

The present invention further provides the compound of the formula (I) in crystalline form of polymorph I

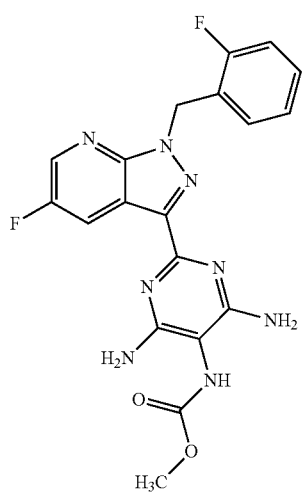

(I)

characterized in that the IR spectrum of the compound exhibits band maxima at 1707, 1633, 1475 $cm^{-1}$.

The present invention further provides the compound of the formula (I) in polymorph (I) as described above, characterized in that the IR spectrum of the compound exhibits band maxima at 1707, 1633, 1566, 1475, 1255, 1223 $cm^{-1}$.

The invention further provides a process for preparing the compound of the formula (I) in crystalline form of polymorph I, characterized in that the compound of the formula (I), present in one or more polymorphs or as a solvate in an inert solvent, is stirred at a temperature of 20° C.-120° C. and the compound of the formula (I) is isolated in crystalline polymorph I.

Preferred solvents for the process for preparing the compound of the formula (I) in crystalline form of polymorph I are a mixture of ethyl acetate/ethanol/water, isopropanol, a mixture of isopropanol/water, methanol, a mixture of methanol/water, acetonitrile, acetone, tetrahydrofuran and methyl tert-butyl ether.

A preferred temperature range for the process for preparing the compound of the formula (I) in crystalline form of polymorph I is from 20° C. to 90° C.

The present invention further provides a compound of the formula (I) in polymorph (I) as described above for treatment of disorders.

The present invention further provides a medicament comprising a compound of the formula (I) in polymorph (I) as described above and no greater proportions of any other form of the compound of the formula (I) in polymorph (I) as described above. The present invention further provides a medicament comprising a compound of the formula (I) in polymorph (I) as described above in more than 90 percent by weight based on the total amount of the compound of the formula (I) present in polymorph (I) as described above.

The present invention further provides for the use of the compound of the formula (I) in polymorph (I) as described above for production of a medicament for treatment of cardiovascular disorders.

The present invention further provides the method for treatment of cardiovascular disorders by administering an effective amount of a compound of the formula (I) in polymorph (I) as described above.

The present invention further provides the compound of the formula (I) as the di-dimethyl sulphoxide solvate

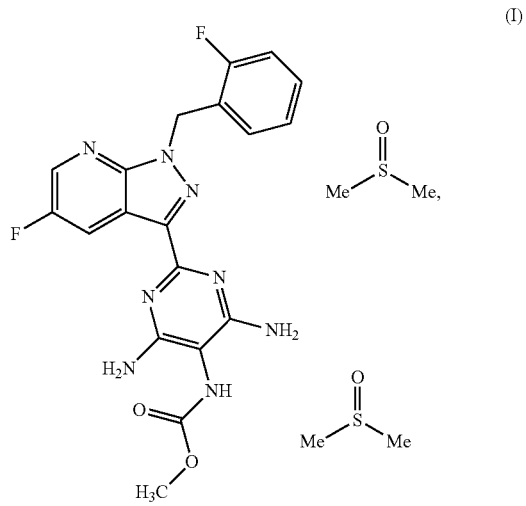

(I)

characterized in that the x-ray diffractogram of the compound exhibits peak maxima of the 2 theta angle at 18.8, 20.3, 21.7.

The present invention further provides the compound of the formula (I) as the di-dimethyl sulphoxide solvate, characterized in that the x-ray diffractogram of the compound exhibits peak maxima of the 2 theta angle at 12.0, 16.6, 17.8, 18.8, 20.3, 21.7.

The present invention further provides the compound of the formula (I) as the di-dimethyl sulphoxide solvate characterized in that the IR spectrum of the compound exhibits band maxima at 1720, 1628, 1481 $cm^{-1}$.

The present invention further provides the compound of the formula (I) as the di-dimethyl sulphoxide solvate, characterized in that the IR spectrum of the compound exhibits band maxima at 1720, 1628, 1481, 1234, 1041, 1017 $cm^{-1}$.

The present invention further provides a process for preparing the compound of the formula (I) as the di-dimethyl sulphoxide solvate in crystalline form, characterized in that the compound of the formula (I), present in one or more polymorphs or as a solvate in dimethyl sulphoxide or a mixture of dimethyl sulphoxide and an inert solvent, for example ethyl acetate, is stirred at a temperature of 20-120° C. and the di-dimethyl sulphoxide solvate is isolated. Preference is given to a temperature range of 20 to 90° C.

The present invention further provides the compound of the formula (XIV)

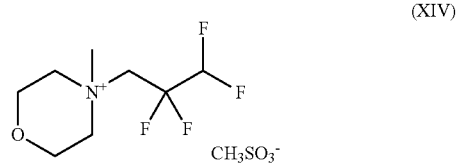

(XIV)

and the salts, solvates and solvates of the salts thereof.

The present invention further provides the compound of the formula (XV)

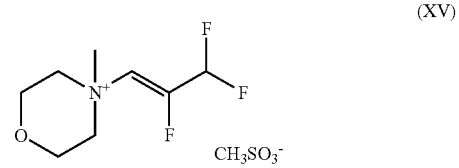

(XV)

and the salts, solvates and solvates of the salts thereof.

A. EXAMPLES

| Abbreviations: | |
|---|---|
| Ac | acetyl |
| CI | chemical ionization (in MS) |
| DCI | direct chemical ionization (in MS) |
| DMF | dimethylformamide |
| DMSO | dimethyl sulphoxide |
| eq. | equivalent(s) |
| ESI | electrospray ionization (in MS) |
| Et | ethyl |
| GC/MS | gas chromatography-coupled mass spectrometry |
| sat. | saturated |
| h | hour(s) |
| HPLC | high-pressure high-performance liquid chromatography |
| HV | high vacuum |
| conc. | concentrated |
| LC/MS | liquid chromatography-coupled mass spectrometry |
| Me | methyl |
| min | minute(s) |
| MS | mass spectrometry |
| NMR | nuclear magnetic resonance spectroscopy |
| rac | racemic/racemate |
| $R_f$ | retention factor (in thin layer chromatography on silica gel) |
| RT | room temperature |
| $R_t$ | retention time (in HPLC) |
| SFC | supercritical fluid chromatography |
| THF | tetrahydrofuran |
| UV | ultraviolet spectrometry |
| v/v | volume to volume ratio (of a solution) |

All X-Ray Diffractometry Data were Obtained with the Following Acquisition Parameters:

| Diffractometer system | PANalytical XPERT-PRO |
|---|---|
| Scan axis | Gonio |
| Anode material | Cu |
| K-Alpha1 [Å] | 1.54060 |
| K-Alpha2 [Å] | 1.54443 |
| K-A2/K-A1 ratio | 0.50000 |
| Scan Mode: | Transmission |
| Scan type: | 2theta: omega |
| 2theta figure: | ±0.2° |

All Infrared Spectroscopy Data were Obtained with the Following Acquisition Parameters:

Spectrometer: Perkin Elmer Spectrum One with diamond ATR unit

Parameter: 32 scans

Resolution: 2 cm$^{-1}$

Example 1

2,2,3,3-Tetrafluoropropyl trifluoromethanesulphonate

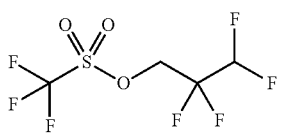

Method A:

252.5 g (0.895 mol) of trifluoromethanesulphonic anhydride were heated to 40° C. and, at this temperature, 130.0 g (0.984 mol) of 2,2,3,3-tetrafluoro-1-propanol were metered in while cooling. After the metered addition had ended, the reaction mixture was heated to 70°-75° C. and stirred for 2 h. The mixture was cooled to 20° C. and the reaction solution was used without further purification in the reaction for Example 2.

Method B:

50.0 g (0.379 mol) of 2,2,3,3-tetrafluoro-1-propanol were cooled to 0° C. and 106.8 g (0.379 mol) of trifluoromethanesulphonic anhydride were added dropwise at 0°-4° C. Subsequently, the reaction mixture was stirred at 25° C. for 2 h, heated to 70°-75° C. and stirred for 2 h. The mixture was cooled to 20° C. and the reaction solution was distilled at 116°-118° C. This gave 85.1 g (85.1% of theory) of the title compound.

$^1$H NMR (400 MHz, CDCl$_3$): δ=4.69 (t, J=11.86 Hz, 2H) 5.54-6.23 (m, 1H) ppm.

Example 2

4-(2,2,3,3-Tetrafluoropropyl)morpholine

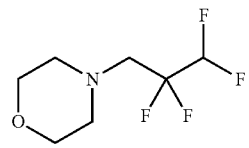 [SMILES: FC(F)C(F)(F)CN1CCOCC1]

Method A:

311.9 g (3.58 mol) of morpholine were dissolved in 290 ml of dichloromethane and cooled to −15° C. At −15°-0° C., 371.4 g (max. 0.895 mol) of the reaction solution from Example 1 were added dropwise while cooling and then the mixture was stirred at 0°-5° C. for 30 min The reaction mixture was heated to 40° C. and stirred for 4.5 h. After cooling to 20° C., 320 ml of water were added and the phases were separated. The organic phase was washed three times with 190 ml each time of water and concentrated on a rotary evaporator at 30° C./30 mbar. The residue (160.7 g) was distilled at 67°-68° C./18 mbar. This gave 151.7 g (84.3% of theory) of the title compound.

$^1$H NMR (400 MHz, CDCl$_3$): δ=2.53-2.70 (m, 4H) 2.89 (tt, J=14.03, 1.74 Hz, 2H) 3.61-3.78 (m, 4H) 5.83-6.22 (m, 1H) ppm.

Method B:

158.5 g (1.82 mol) of morpholine were cooled to 5° C. At 5°-10° C., 189.5 g (max. 0.455 mol) of the reaction solution from Example 1 were added dropwise while cooling and then the mixture was stirred at 5°-10° C. for 30 min. The reaction mixture was heated to 40° C. and stirred for 1 h. After cooling to 20° C., 160 ml of water and 160 ml of toluene were added and the phases were separated. The organic phase was washed with 160 ml of water and concentrated on a rotary evaporator at 50° C./50 mbar. The residue (81.0 g) was distilled at 67°-68° C./18 mbar. This gave 77.0 g (84.1% of theory) of the title compound.

Example 3

4-Methyl-4-(2,2,3,3-tetrafluoropropyl)morpholin-4-ium methanesulphonate

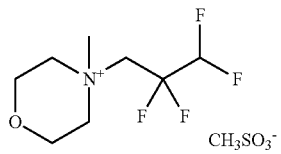

Method A:

143.7 g (1.31 mol) of methyl methanesulphonate were heated to 135° C. and, at this temperature, 250.0 g (1.243 mol) of the compound from Example 2 were added dropwise. Subsequently, the mixture was stirred at 100° C. for 22 h. The reaction mixture was cooled to 85° C. and 375 ml of isopropanol were added. After cooling to 0°-5° C., the mixture was stirred for a further 30 min and the product was filtered off with suction. The product was washed three times with 125 ml each time of isopropanol and dried in a vacuum drying cabinet at 45° C. under a gentle nitrogen stream. This gave 336.8 g (87.1% of theory) of the title compound.

$^1$H NMR (400 MHz, D$_2$O): δ=2.81 (s, 3H) 3.55 (s, 3H) 3.68-3.93 (m, 4H) 4.01-4.24 (m, 4H) 4.33-4.51 (m, 2H) 6.13-6.48 (m, 1H) ppm.

Method B:

20.0 g (181.3 mmol) of methyl methanesulphonate were heated to 135° C. and, at this temperature, 35.1 g (172.7 mmol) of the compound from Example 2 were added dropwise. The mixture was stirred at 135° C. for 3 h and then 40 ml of water were added. After cooling to 50° C., the aqueous solution of the title compound was used in the subsequent stage (see Example 4).

Example 4

4-Methyl-4-[2,3,3-trifluoroprop-1-en-1-yl]morpholin-4-ium methanesulphonate

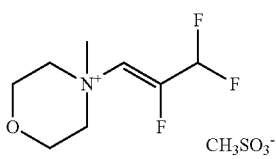

16.9 g (189.9 mmol) of 45% sodium hydroxide solution were metered into the aqueous solution of the compound from Example 3, Method B (max. 172.7 mmol) at 50°-55° C., and the mixture was stirred at 50° C. for 1 h. The reaction mixture was cooled to 20° C. and the precipitated salts were filtered off with suction and washed with 5 ml of water. The aqueous product solution (102.1 g; max. 172.7 mmol) was used in the subsequent stage (see Example 5).

For analytical purposes, a sample was concentrated and dried.

$^1$H NMR (400 MHz, D$_2$O): δ=2.81 (s, 3H) 3.59 (s, 3H) 3.76-3.85 (m, 2H) 3.97-4.09 (m, 4H) 4.12-4.20 (m, 2H) 6.39-6.69 (m, 1H) 6.74-6.83 (m, 1H) ppm.

Example 5

2-Fluoro-3-(morpholin-4-yl)acrylaldehyde

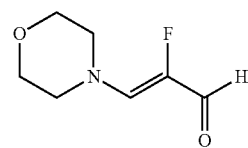 [SMILES: O=C/C(F)=C/N1CCOCC1]

Method A:

An aqueous solution of the compound from Example 4 (max. 251.5 mmol) was heated to 75° C. Subsequently, 43.8 g (503 mmol) of morpholine and 76.3 g (755 mmol) of triethylamine were added dropwise. The mixture was stirred at 75° C. for 2 h and cooled to 23° C., and 290 ml of dichloromethane and 100 ml of triethylamine were added. The phases were separated, the aqueous phase was washed with a mixture of 290 ml of dichloromethane and 100 ml of triethylamine, and the combined organic phases were filtered, washed with 250 ml of sat. aqueous potassium carbonate solution and concentrated on a rotary evaporator at 40° C. 50 ml of toluene were added and the mixture was concentrated further. This gave 34.2 g (81.9% of theory) of the title compound.

Method B:

A mixture of 43.8 g (503 mmol) of morpholine and 76.3 g (755 mmol) of triethylamine was heated to 75° C. and an aqueous solution of the compound from Example 4 (max. 251.5 mmol) was added dropwise within 25 min. Subsequently, the mixture was stirred at 75° C. for 2 h and cooled to 23° C., and 290 ml of dichloromethane and 100 ml of triethylamine were added. The mixture was filtered, the phases were separated, the aqueous phase was washed with a mixture of 290 ml of dichloromethane and 100 ml of triethylamine, and the combined organic phases were washed with 250 ml of sat. aqueous potassium carbonate solution and concentrated on a rotary evaporator at 40° C. 50 ml of toluene were added and the mixture was concentrated further. This gave 35.3 g (83.4% of theory) of the title compound.

$^1$H NMR (500 MHz, CDCl$_3$): δ=3.51-3.60 (m, 4H) 3.72-3.83 (m, 4H) 6.16 (d, J=27.1 Hz, 1H) 8.59 (d, J=18.9 Hz, 1H) ppm.

Method C:

A mixture of 30.2 g (345.3 mmol) of morpholine and 52.5 g (518.0 mmol) of triethylamine was heated to 75° C. and the aqueous solution of the compound from Example 4, Method B (max. 172.7 mmol) was added dropwise at 75°-80° C. The mixture was stirred under reflux for 2 h, cooled to 23° C. and washed with 100 ml of dichloromethane. The aqueous phase was washed twice with a mixture of 100 ml of dichloromethane and 15 ml of triethylamine, and the combined organic phases were washed with 85 ml of sat. aqueous potassium carbonate solution and concentrated under reduced pressure at 45°-50° C. 120 ml of toluene and 60 ml of toluene were distilled off. The suspension was stirred at room temperature overnight, and the product was filtered off with suction and dried in a vacuum drying cabinet at 50° C. under a gentle nitrogen stream. This gave 19.2 g (68.3% of theory) of the title compound.

Example 6

Ethyl 5-fluoro-1-(2-fluorobenzyl)-1H-pyrazolo[3,4-b]pyridine-3-carboxylate

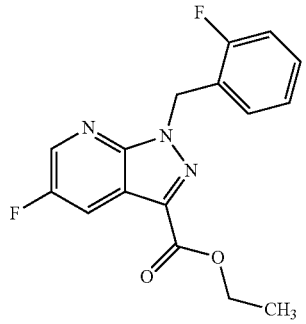 [SMILES: CCOC(=O)c1nn(Cc2ccccc2F)c2ncc(F)cc12]

Method A:

22.3 g (84.8 mmol) of ethyl 5-amino-1-(2-fluorobenzyl)-1H-pyrazole-3-carboxylate (preparation described for Example 20A in WO 00/06569) were initially charged in 59.5 ml of ethanol, and 11.0 ml (169.6 mmol) of methanesulphonic acid, 9.0 g (212.1 mmol) of lithium chloride and 15.0 g (84.8 mmol) of the compound from Example 5 were added at RT. The mixture was stirred at reflux temperature for 4.5 h. After cooling to room temperature, the product was filtered off with suction, washed twice with 4.5 ml of ethanol and stirred with 325 ml of water for 1 h. The solids were filtered off with suction, washed twice with 11.5 ml of water and dried in a vacuum drying cabinet at 50° C. under a gentle nitrogen stream. This gave 21.8 g (81.0% of theory) of the title compound.

MS (ESIpos): m/z=318 (M+H)$^+$ $^1$H NMR (400 MHz, DMSO-d$_6$): δ=1.37 (t, 3H), 4.40 (q, 2H), 5.86 (s, 2H), 7.15-7.27 (m, 3H), 7.36-7.41 (m, 1H), 8.25 (d, 1H), 8.78 (s br., 1H) ppm.

Method B:

27.0 g (635.2 mmol) of lithium chloride and 42.2 g (254.1 mmol) of the compound from Example 5 were initially charged in 75 ml of ethanol and heated to reflux temperature. At this temperature, a solution of 66.9 g (254.1 mmol) of ethyl 5-amino-1-(2-fluorobenzyl)-1H-pyrazole-3-carboxylate (preparation described for Example 20A in WO 00/06569) and 33.0 ml (508.2 mmol) of methanesulphonic acid in 180 ml of ethanol were added within 10 min. The mixture was stirred at reflux temperature for 2 h, then 120 ml of isopropanol were added, the mixture was cooled to 62° C., 0.6 g of the title compound were used for seeding and the mixture was cooled to 5° C. within 4 h. The product was filtered off with suction, stirred with 120 ml of isopropanol, filtered off with suction, washed with 180 ml of water, stirred with 300 ml of water for 0.5 h, filtered off with suction, washed with 300 ml of water and dried in a vacuum drying cabinet at 50° C. under a gentle nitrogen stream. This gave 65.1 g (80.7% of theory) of the title compound.

Method C:

5.42 g (20.6 mmol) of ethyl 5-amino-1-(2-fluorobenzyl)-1H-pyrazole-3-carboxylate (preparation described for Example 20A in WO 00/06569) were initially charged in 20 ml of ethanol, and 1.5 g (41.1 mmol) of hydrogen chloride were introduced. This solution was metered into 3.42 g (20.6 mmol) of the compound from Example 5 in 50 ml of ethanol at reflux temperature within 10 min The mixture was stirred at reflux temperature for 2 h, then 10 ml of isopropanol were added and the mixture was cooled to 5° C. The product was filtered off with suction, washed with 10 ml of isopropanol and dried in a vacuum drying cabinet at 50° C. under a gentle nitrogen stream. This gave 4.84 g (74.2% of theory) of the title compound.

Example 7

5-Fluoro-1-(2-fluorobenzyl)-1H-pyrazolo[3,4-b]pyridine-3-carboxamide

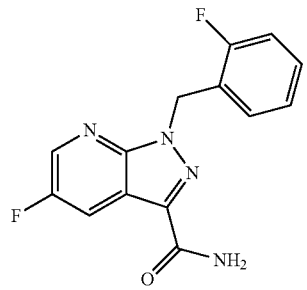 [SMILES: NC(=O)c1nn(Cc2ccccc2F)c2ncc(F)cc12]

10 ml of ethanol, 14.9 ml (441.2 mmol) of formamide and 3.6 g (66.2 mmol) of sodium methoxide solution in methanol (30%) were added to 7.0 g (22.1 mmol) of the compound obtained in Example 6. The reaction mixture was heated to 95°-100° C. and the low boilers were distilled off. The mixture was stirred at 125° C. for 1.5 h, 30 ml of water were added, and the mixture was cooled to room temperature and stirred for 1 h. The precipitated solids were filtered off with suction, washed three times with 8.5 ml each time of water and dried in a vacuum drying cabinet at 45° C. under a gentle nitrogen stream. This gave 6.2 g (97.5% of theory) of the title compound.

MS (ESIpos): m/z=289 (M+H)$^+$ $^1$H NMR (400 MHz, DMSO-d$_6$): δ=5.87 (s, 2H), 7.12-7.26 (m, 3H), 7.34-7.40 (m, 1H), 7.60 (s br., 1H), 7.87 (s br., 1H), 8.28 (dd, 1H), 8.72 (dd, 1H) ppm.

Example 8

5-Fluoro-1-(2-fluorobenzyl)-1H-pyrazolo[3,4-b]pyridine-3-carbonitrile

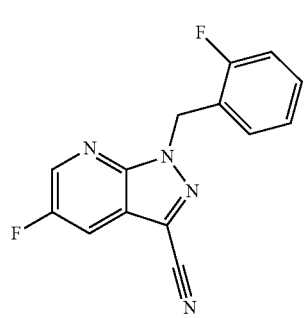 [SMILES: N#Cc1nn(Cc2ccccc2F)c2ncc(F)cc12]

17.3 g (60.0 mmol) of the compound obtained in Example 7 were heated to 103°-107° C. in 40.5 ml of sulpholane and 5.4 ml of acetonitrile. Thereafter, 6.9 g (45.0 mmol) of phosphorus oxychloride were slowly added dropwise while stirring, the dropping funnel was rinsed with 2.8 ml of acetonitrile, then the mixture was stirred at 107° C. for 1.5 h until conversion was complete (HPLC). Thereafter, the mixture was cooled to room temperature, and 2.8 ml of sulpholane/acetonitrile (5:1 vol/vol) and then 17.8 ml of water were added dropwise. The mixture was stirred for 0.5 h, a solution of 9.4 g of aqueous ammonia (28%) in 22.7 ml of water was added dropwise and the mixture was stirred for a further 2 h. The precipitated solids were filtered off with suction, washed three times with 20.5 ml each time of water and dried in a vacuum drying cabinet at 50° C. under a gentle nitrogen stream. This gave 14.7 g (91.9% of theory) of the title compound.

MS (ESIpos): m/z=271 (M+H)+

$^1$H NMR (400 MHz, DMSO-$d_6$): δ=5.87 (s, 2H), 7.17-7.42 (m, 4H), 8.52 (dd, 1H), 8.87 (dd, 1H) ppm.

Example 9

5-Fluoro-1-(2-fluorobenzyl)-1H-pyrazolo[3,4-b]pyridine-3-carboximidamide hydrochloride

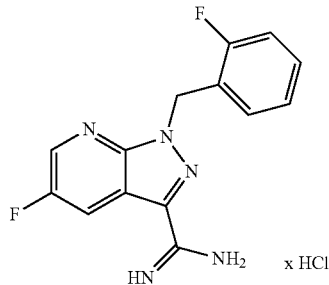 [SMILES: N=C(N)c1nn(Cc2ccccc2F)c2ncc(F)cc12]

406.0 g (1.50 mol) of the compound from Example 8 were suspended in 2.08 l of ethanol. Subsequently, 54.1 g (0.30 mol) of sodium methoxide in methanol (30%) were added and the mixture was stirred at room temperature overnight. 88.4 g (1.65 mol) of ammonium chloride were added, and the mixture was heated to 65° C. and stirred at 65° C. for 3.5 h. The solvents were distilled off and the residue was stirred with 1.6 l of ethyl acetate overnight. The precipitated solids were filtered off with suction, washed twice with 140 ml each time of ethyl acetate and dried in a vacuum drying cabinet at 50° C. under a gentle nitrogen stream. This gave 441.4 g (90.7% of theory) of the title compound.

MS (ESIpos): m/z=288 (M+H)+

$^1$H NMR (400 MHz, DMSO-$d_6$): δ=5.90 (s, 2H), 7.15-7.20 (m, 1H), 7.22-7.28 (m, 1H), 7.29-7.35 (m, 1H), 7.36-7.43 (m, 1H), 8.48 (dd, 1H), 8.86 (dd, 1H), 9.35 (br. s, 3H) ppm.

Example 10

[(E)-phenyldiazenyl]malononitrile

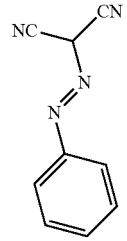 [SMILES: N#CC(C#N)/N=N/c1ccccc1]

Method A:

262 g of conc. hydrochloric acid (2.59 mol) and 117.5 ml of water were added dropwise at 0°-5° C. to 1525 ml of water and 117.5 g (1.26 mol) of aniline. Subsequently, a solution of 87.1 g (1.26 mol) of sodium nitrite in 222.5 ml of water was added dropwise within 1 h and rinsed in with 60 ml of water, and the mixture was stirred at 0°-5° C. for 15 min Thereafter, at this temperature, a solution of 131.4 g (1.60 mol) of sodium acetate in 665 ml of water (19 ml) was added dropwise within 45 min and rinsed in with 60 ml of water, and a solution of 83.4 g (1.26 mol) of malononitrile in 233 ml of ethanol was added dropwise within 1 h. 68.5 ml of ethanol were used to rinse it in, and the mixture was stirred at 0°-5° C. for 2 h. The yellow solids were filtered off with suction and washed three times with 625 ml each time of water and with 488 ml of cold toluene. The still-moist residue was dissolved in 872 g of DMF. This gave 1117.0 g of DMF solution of the title compound.

Method B:

87.4 g of conc. hydrochloric acid (0.86 mol) and 39.5 ml of water were added dropwise at 0°-5° C. to 508.5 ml of water and 39.2 g (0.42 mol) of aniline Subsequently, a solution of 29.0 g (0.42 mol) of sodium nitrite in 74.5 ml of water was added dropwise within 1 h and rinsed in with 20 ml of water, and the mixture was stirred at 0°-5° C. for 15 min. Thereafter, at this temperature, a solution of 43.8 g (0.54 mol) of sodium acetate in 221.5 ml of water was added dropwise within 45 min and rinsed in with 20 ml of water, and a solution of 27.8 g (0.42 mol) of malononitrile in 77.5 ml of ethanol was added dropwise within 1 h. 23 ml of ethanol were used to rinse it in, and the mixture was stirred at 0°-5° C. for 2 h. The yellow solids were filtered off with suction and washed three times with 208.5 ml each time of water and with 162.5 ml of cold toluene. 103.1 g of moist product were obtained. 13.8 g of the moist product were dissolved in 13.9 g of sulpholane. This gave 27.7 g of sulpholane solution of the title compound.

Example 11

2-[5-Fluoro-1-(2-fluorobenzyl)-1H-pyrazolo[3,4-b]pyridin-3-yl]-5-[(E)-phenyldiazenyl]pyrimidine-4,6-diamine

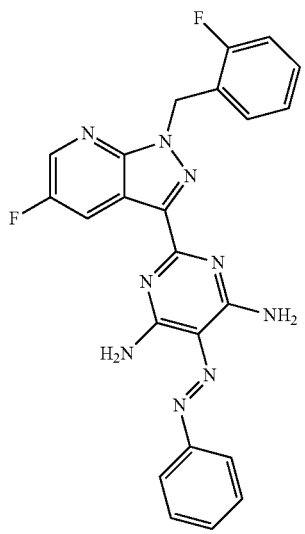 [SMILES: Nc1nc(-c2nn(Cc3ccccc3F)c3ncc(F)cc23)nc(N)c1/N=N/c1ccccc1]

Method A:

448.2 g (1.38 mol) of the compound from Example 9 were suspended in 1059 ml of DMF. The mixture was heated to 85° C. and 212 ml (1.52 mol) of triethylamine were added dropwise at this temperature. Subsequently, 1751 g of the DMF solution from Example 10 were added dropwise within 20 min and rinsed in with 490 ml of DMF, and the mixture was stirred at 100° C. overnight. The reaction mixture was cooled to RT, 656 ml of water were added dropwise and the mixture was stirred at RT for 0.5 h, then cooled to 0°-5° C. and stirred for a further 1 h. The solids were filtered off with suction, washed twice, each time with a solution of 1443 g of water and 236 g of methanol, and then washed with 586 ml of methanol, suction-dried and dried in a vacuum drying cabinet at 50° C. under a gentle nitrogen stream. This gave 522.2 g (82.5% of theory) of the title compound.

$^1$H NMR (400 MHz, DMSO-d$_6$): δ=5.84 (s, 2H) 7.14-7.28 (m, 3H) 7.34-7.41 (m, 2H) 7.46-7.52 (m, 2H) 7.95 (br. s, 2H) 8.02 (dd, 2H) 8.50 (br. s, 2H) 8.70-8.73 (m, 1H) 9.02-9.06 (m, 1H) ppm.

Method B:

30.0 g (92.7 mmol) of the compound from Example 9 were suspended in 72 ml of DMF. The mixture was heated to 100° C. and a mixture of 14.2 ml (101.9 mmol) of triethylamine and 150 g of the DMF solution from Example 10 was added dropwise at this temperature within 30 min. 30 ml of DMF were used to rinse it in and the mixture was stirred at 100° C. for 20 h. The reaction mixture was cooled to 95°-90° C., 24 ml of water were added dropwise within 10 min, then the mixture was cooled to 0°-5° C. within 1.5 h and stirred for 1 h. The solids were filtered off with suction, washed with a solution of 60 g of water and 60 g of dimethylformamide, washed twice, each time with a solution of 50 g of water and 50 g of methanol, and then with 40 ml of methanol, suction-dried and dried in a vacuum drying cabinet at 50° C. under a gentle nitrogen stream. This gave 35.5 g (83.7% of theory) of the title compound.

Method C:

11.7 g (36.0 mmol) of the compound from Example 9 were suspended in 15.6 ml of sulpholane. The mixture was heated to 100° C. and a mixture of 5.5 ml (39.6 mmol) of triethylamine and 27.7 g of the sulpholane solution from Example 10 Method B was added dropwise at this temperature within 35 min. 2 ml of sulpholane were used to rinse it in and the mixture was stirred at 100° C. for 2.5 h. The reaction mixture was cooled to 60° C., 90 ml of isopropanol were added dropwise, then the mixture was cooled to 0°-5° C. within 15 min and stirred for 2.5 h. The solids were filtered off with suction, washed three times, each time with 50 g of water and 24 ml of isopropanol, suction-dried and dried in a vacuum drying cabinet at 50° C. under a gentle nitrogen stream. This gave 14.2 g (85.9% of theory) of the title compound.

Example 12

2-[5-Fluoro-1-(2-fluorobenzyl)-1H-pyrazolo[3,4-b]pyridin-3-yl]pyrimidine-4,5,6-triamine

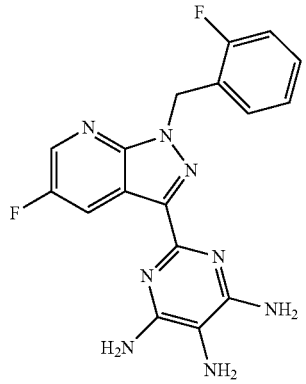 [SMILES: Nc1nc(-c2nn(Cc3ccccc3F)c3ncc(F)cc23)nc(N)c1N]

Method A:

182.0 g (0.39 mol) of the compound from Example 11 were initially charged in 1.82 l of DMF and then 4.2 g of palladium (5% on carbon, 50% water-moist) were added. Hydrogenation was effected at 60° C. and hydrogen pressure 60 bar while stirring overnight. The mixture was filtered through kieselguhr and washed through with 150 ml of DMF and then with 150 ml of methanol, and concentrated at 60°-70° C. down to a weight of 425 g of distillation residue. The residue was heated to 75°-80° C., 300 ml of methanol were added dropwise at this temperature and the mixture was stirred for 15 min. The mixture was cooled to RT within 1 h, then 1290 ml of water were added dropwise and the mixture was stirred overnight. The solids were filtered off with suction, washed twice with 500 ml each time of water, suction-dried and dried in a vacuum drying cabinet at 50° C. under a gentle nitrogen stream. This gave 159.7 g of the title compound. The product has a content of 73.7% by weight and 12.4% by weight of DMF (80.3% of theory) and was used thus in the subsequent stage. According to the intensity of the water wash, the DMF content was in the range of 10-17% by weight.

Method B:

25.0 g of the DMF-containing solids from Method A were suspended in 220 ml of water and filtered with suction through a suction filter. The solids were washed four times on the suction filter with 100 ml each time of water at 95° C., suction-dried and dried in a vacuum drying cabinet at 50° C. under a gentle nitrogen stream. This gave 21.2 g of the DMF-free title compound.

MS (ESIpos): m/z=369 (M+H)$^+$

For analytical purposes, a sample was purified by means of silica gel filtration:

$^1$H NMR (400 MHz, DMSO-d$_6$): δ=4.04 (br. s, 2H) 5.75 (s, 2H) 5.86 (br. s, 4H) 7.10-7.26 (m, 3H) 7.32-7.39 (m, 1H) 8.61-8.64 (m, 1H) 8.85 (dd, 1H) ppm.

Example 13

Methyl{4,6-diamino-2-[5-fluoro-1-(2-fluorobenzyl)-1H-pyrazolo[3,4-b]pyridin-3-yl]pyrimidin-5-yl}carbamate

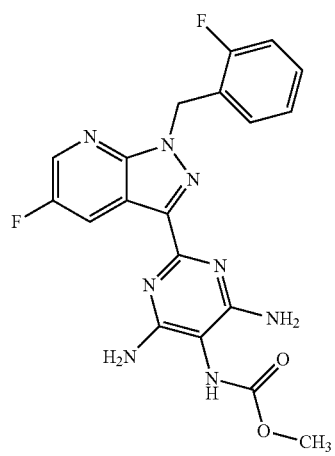 [SMILES: COC(=O)Nc1c(N)nc(-c2nn(Cc3ccccc3F)c3ncc(F)cc23)nc1N]

Method A:

4.0 g (77.0% by weight, 8.36 mmol) of the compound from Example 12 in 37.9 ml of isopropanol were heated to 35° C. and then 0.84 ml (10.87 mmol) of methyl chloroformate was added dropwise. The mixture was stirred at 35°-40° C. for 20 h and heated to 50° C., and 9.5 ml of methanol were added. Subsequently, 1.9 ml of triethylamine were added dropwise within 0.5 h and rinsed in with 1.3 ml of methanol, and the mixture was stirred at 50° C. for 1 h. Thereafter, the reaction mixture was cooled to RT and stirred at RT for 1 h, and the solids were filtered off with suction, washed three times with 8 ml each time of ethanol, suction-dried and dried in a vacuum drying cabinet at 50° C. under a gentle nitrogen stream. This gave 3.4 g of crude product. 3.0 g of the crude product were stirred in 8 ml of DMSO for 5 min, 13.0 ml of ethyl acetate and 50 mg of activated carbon were added, and the mixture was heated at reflux (84° C.) for 15 min. The suspension was hot-filtered and the filter residue was washed with 1.9 ml of ethyl acetate[1]. 60 ml of ethyl acetate and 16 ml of ethanol were heated to 60° C., and the combined filtrates were added dropwise and stirred at 60° C. for 1.5 h. The suspension was cooled to RT within 25 min, stirred for a further 1.5 h, cooled further to 0°-5° C. and stirred for a further 1 h. The solids were filtered off with suction, washed twice with 6.4 ml each time of ethyl acetate, suction-dried and dried in a vacuum drying cabinet at 50° C. under a gentle nitrogen stream. This gave 2.2 g (70.0% of theory) of the title compound.

[1] According to the preparation process described, the di-dimethyl sulphoxide solvate is obtained at this point, and this is characterized in Tables 2 and 4 by the reflections in the x-ray diffractogram and bands in the IR spectrum.

MS (ESIpos): m/z=427 (M+H)$^+$ $^1$H NMR (400 MHz, DMSO-d$_6$): δ=3.62 (br s, 3H), 5.79 (s, 2H), 6.22 (br s, 4H), 7.10-7.19 (m, 2H), 7.19-7.26 (m, 1H), 7.32-7.40 (m, 1H), 7.67 and 7.99 (2 br s, 1H), 8.66 (m, 1H), 8.89 (dd, 1H) ppm.

The di-dimethyl sulphoxide solvate of the compound of the formula (I) has the advantage of much better filterability than the substance in the prior art. Furthermore, the preparation process via the di-dimethyl sulphoxide solvate of the compound of the formula (I) leads to a very high purity of the compound of the formula (I).

Method B:

4.0 g (10.8 mmol) of the compound from Example 12 Method B in 37.9 ml of isopropanol were heated to 35° C. and then 1.1 ml (14.1 mmol) of methyl chloroformate were added dropwise. The mixture was stirred at 35°-40° C. for 16.5 h and cooled to RT, and 2.1 ml of aqueous ammonia (28%) were added. Subsequently, 4.2 ml of water were added and the mixture was stirred for 2.5 h. The solids were filtered off with suction, washed twice with 5 ml each time of water, suction-dried and dried in a vacuum drying cabinet at 50° C. under a gentle nitrogen stream. This gave 4.4 g of crude product.

Method C:

4.0 g (10.8 mmol) of the compound from Example 12 Method B in 37.9 ml of isopropanol were heated to 35° C. and then 1.1 ml (14.1 mmol) of methyl chloroformate were added dropwise. The mixture was stirred at 35°-40° C. for 16.5 h, and 9.5 ml of methanol were added at 50° C. Subsequently, 2.42 ml of triethylamine were added dropwise within 20 min and rinsed in with 1.3 ml of methanol, and the mixture was stirred at 50° C. for 1 h. Thereafter, the reaction mixture was cooled to RT and stirred at RT for 1 h, and the solids were filtered off with suction, washed three times with 8 ml each time of methanol, suction-dried and dried in a vacuum drying cabinet at 50° C. under a gentle nitrogen stream. This gave 4.3 g of crude product.

Method D:

6.9 g of the crude product were stirred in 18.4 ml of DMSO for 5 min, 30.0 ml of ethyl acetate and 115 mg of activated carbon were added, and the mixture was heated at reflux (84° C.) for 15 min. The suspension was hot-filtered and the filter residue was washed with 4.4 ml of ethyl acetate. 138 ml of ethyl acetate were heated to 50° C., and the combined filtrates were added dropwise and stirred at 45-50° C. for 1 h. The suspension was cooled to 0°-5° C. within 1.5 h and stirred for a further 1 h. The solids were filtered off with suction, washed twice with 14.8 ml each time of ethyl acetate and suction-dried for 1 h. 6.4 g of the di-dimethyl sulphoxide solvate were obtained as a moist product[1].

Method E:

2.0 g of the di-dimethyl sulphoxide solvate were stirred at reflux temperature in 40 ml of ethyl acetate and 11.1 ml of ethanol for 17 h, cooled to RT and stirred for a further 1 h. The solids were filtered off with suction, washed four times with 1.4 ml each time of ethyl acetate and dried in a vacuum drying cabinet at 50° C. under a gentle nitrogen stream. This gave 1.4 g of the title compound present in polymorph I.

Method F:

0.5 g of the di-dimethyl sulphoxide solvate were stirred at reflux temperature in 12.5 ml of solvent for 17 h, cooled to RT and stirred for a further 1 h. The solids were filtered off with suction, washed with 2 ml of solvent and suction-dried for 30 min. This gave 0.3 g of the title compound present in polymorph I.

The following solvents were used:

1.) 9 ml of ethyl acetate/3.5 ml of ethanol/0.3 ml of water

2.) 12.5 ml of isopropanol

3.) 12.5 ml of isopropanol/0.3 ml of water

4.) 12.5 ml of methanol

5.) 12.5 ml of methanol/0.3 ml of water

6.) 12.5 ml of acetonitrile

7.) 12.5 ml of acetone

8.) 12.5 ml of tetrahydrofuran,

9.) 12.5 ml of methyl tert-butyl ether

Table 1 indicates the reflections of the x-ray diffractogram. Table 3 shows the bands of the IR spectrum.

The compound (I) in crystalline polymorph I is notable for higher stability and more particularly for the fact that it is stable in the micronization process and hence no conversion and recrystallization takes place.

The compound of the formula (I) can be prepared by processes described above. This affords the compound of the formula (I) in a crystal polymorph referred to hereinafter as polymorph I. Polymorph I has a melting point of 257° C. and a characteristic x-ray diffractogram featuring the reflections (2 theta) 5.9, 6.9, 16.2, 16.5, 24.1 and 24.7, and a characteristic IR spectrum featuring the band maxima (in cm$^{-1}$) 1707, 1633, 1566, 1475, 1255 and 1223 (Tables 1 and 3, FIGS. 1 and 5).

Surprisingly, four further polymorphs, a monohydrate, a dihydrate, a DMF/water solvate and a di-dimethyl sulphoxide solvate, and also a triacetic acid solvate of the compound of the formula (I) were found. The compound of the formula (I) in polymorph II melts at approx. 253° C.; the compound of the formula (I) in polymorph III has a melting point of approx. 127° C. Polymorph IV of the compound of the formula I melts at a temperature of 246° C., while polymorph V has a melting point of 234° C. The monohydrate contains approx. 4.1% water, the dihydrate contains 7.8% water, the DMF/water solvate contains 13.6% dimethylformamide and 0.9% water, the di-DMSO solvate contains 26.8% dimethyl sulphoxide and the triacetic acid solvate contains 29.7% acetate. Each of the crystalline forms mentioned has a characteristic x-ray diffractogram and IR spectrum (Tables 2 and 3, FIGS. 1-4, 6-14).

TABLE 1

X-ray diffractometry for polymorphs I to V
Reflections

| Polymorph I [2 theta] | Polymorph II [2 theta] | Polymorph III [2 theta] | Polymorph IV [2 theta] | Polymorph V [2 theta] |
|---|---|---|---|---|
| 5.9 | 4.9 | 6.2 | 6.2 | 3.2 |
| 6.9 | 7.3 | 6.8 | 8.7 | 5.1 |
| 8.3 | 9.7 | 8.7 | 12.4 | 5.4 |
| 10.4 | 9.9 | 9.8 | 15.8 | 6.4 |
| 10.5 | 10.8 | 12.4 | 18.1 | 6.6 |
| 11.3 | 14.3 | 15.8 | 18.6 | 10.2 |
| 11.6 | 14.9 | 17.5 | 19.2 | 10.7 |
| 11.9 | 15.6 | 18.1 | 19.6 | 11.8 |
| 12.2 | 16.5 | 18.6 | 20.2 | 12.8 |
| 14.5 | 18.1 | 19.1 | 20.9 | 13.2 |
| 14.7 | 18.3 | 19.6 | 21.8 | 15.2 |
| 15.1 | 19.6 | 20.1 | 22.3 | 15.5 |
| 16.2 | 21.0 | 21.0 | 23.1 | 15.7 |
| 16.5 | 21.8 | 21.9 | 23.7 | 16.3 |
| 20.0 | 22.4 | 22.8 | 24.2 | 17.0 |
| 21.9 | 23.1 | 23.7 | 26.0 | 17.7 |
| 22.7 | 23.7 | 24.5 | 26.5 | 17.9 |
| 23.5 | 27.1 | 25.3 | 29.2 | 19.6 |
| 24.1 | 28.1 | 25.7 | 31.3 | 22.1 |
| 24.7 |  | 26.8 | 33.8 | 22.8 |
| 25.4 |  | 27.5 |  | 23.5 |
| 25.7 |  | 28.2 |  | 24.4 |
| 26.6 |  | 29.6 |  | 26.3 |
| 28.0 |  | 30.9 |  | 27.9 |
| 30.2 |  | 31.3 |  | 28.3 |
|  |  | 31.6 |  | 29.3 |
|  |  | 32.8 |  | 30.3 |
|  |  | 33.8 |  |  |
|  |  | 34.6 |  |  |

TABLE 2

X-ray diffractometry for polymorph hydrates and solvates
Reflections

| Monohydrate [2 theta] | Dihydrate [2 theta] | DMF/water solvate [2 theta] | di-DMSO solvate [2 theta] | Acetic acid solvate [2 theta] |
|---|---|---|---|---|
| 6.0 | 5.9 | 8.2 | 6.9 | 5.3 |
| 8.5 | 7.9 | 9.2 | 11.0 | 7.2 |
| 9.6 | 8.7 | 9.7 | 12.0 | 9.3 |
| 12.1 | 9.0 | 11.9 | 13.8 | 10.0 |
| 13.6 | 11.8 | 12.5 | 14.1 | 10.7 |
| 15.5 | 13.7 | 12.7 | 15.7 | 11.0 |
| 17.3 | 14.7 | 13.3 | 16.1 | 11.6 |
| 18.2 | 15.8 | 14.1 | 16.2 | 11.9 |
| 19.3 | 16.4 | 15.6 | 16.6 | 12.5 |
| 19.7 | 18.1 | 16.0 | 17.1 | 14.1 |
| 20.2 | 19.3 | 16.5 | 17.7 | 14.4 |
| 20.9 | 19.8 | 16.8 | 17.8 | 14.8 |
| 21.5 | 20.6 | 17.6 | 18.8 | 16.6 |
| 22.2 | 21.7 | 18.3 | 19.9 | 18.0 |
| 23.5 | 21.7 | 19.3 | 20.3 | 18.8 |
| 24.1 | 22.5 | 19.4 | 20.7 | 19.2 |
| 25.7 | 22.7 | 19.6 | 21.3 | 19.4 |
| 26.8 | 22.9 | 19.8 | 21.7 | 19.6 |
| 27.5 | 23.3 | 20.0 | 21.9 | 19.7 |
| 29.4 | 23.7 | 20.5 | 22.4 | 20.1 |
| 30.8 | 24.9 | 20.6 | 22.8 | 20.4 |
| 32.2 | 25.5 | 20.7 | 23.6 | 21.0 |
|  | 26.0 | 21.0 | 24.1 | 21.6 |
|  | 26.8 | 21.8 | 24.4 | 22.9 |
|  | 27.1 | 22.2 | 25.2 | 23.5 |
|  | 27.8 | 22.4 | 25.5 | 24.1 |
|  | 28.9 | 22.8 | 25.9 | 24.4 |
|  | 30.7 | 23.1 | 26.6 | 24.8 |
|  | 31.3 | 23.6 | 26.9 | 25.5 |
|  | 32.0 | 23.9 | 28.9 | 26.5 |
|  |  | 24.8 | 29.9 | 26.8 |
|  |  | 25.2 | 30.9 | 27.7 |

TABLE 2-continued

X-ray diffractometry for polymorph hydrates and solvates
Reflections

| Monohydrate [2 theta] | Dihydrate [2 theta] | DMF/water solvate [2 theta] | di-DMSO solvate [2 theta] | Acetic acid solvate [2 theta] |
|---|---|---|---|---|
|  |  | 25.6 | 33.2 | 31.5 |
|  |  | 25.8 | 33.4 |  |
|  |  | 26.1 | 33.9 |  |
|  |  | 26.7 |  |  |
|  |  | 26.8 |  |  |
|  |  | 27.2 |  |  |
|  |  | 27.6 |  |  |
|  |  | 28.1 |  |  |
|  |  | 28.4 |  |  |
|  |  | 28.6 |  |  |
|  |  | 29.4 |  |  |
|  |  | 29.7 |  |  |
|  |  | 30.3 |  |  |
|  |  | 30.6 |  |  |
|  |  | 31.4 |  |  |
|  |  | 31.5 |  |  |
|  |  | 31.7 |  |  |
|  |  | 32.1 |  |  |
|  |  | 32.4 |  |  |
|  |  | 32.6 |  |  |
|  |  | 32.7 |  |  |
|  |  | 34.1 |  |  |
|  |  | 34.3 |  |  |
|  |  | 34.7 |  |  |
|  |  | 35.6 |  |  |
|  |  | 35.9 |  |  |
|  |  | 36.6 |  |  |

TABLE 3

IR spectra of polymorphs I to V
Band maxima

| Polymorph I [cm$^{-1}$] | Polymorph II [cm$^{-1}$] | Polymorph III [cm$^{-1}$] | Polymorph IV [cm$^{-1}$] | Polymorph V [cm$^{-1}$] |
|---|---|---|---|---|
| 690 | 691 | 697 | 698 | 691 |
| 744 | 752 | 744 | 752 | 745 |
| 761 | 771 | 753 | 773 | 759 |
| 774 | 779 | 773 | 809 | 773 |
| 810 | 810 | 808 | 833 | 809 |
| 845 | 848 | 835 | 873 | 847 |
| 872 | 871 | 873 | 911 | 873 |
| 899 | 903 | 913 | 936 | 896 |
| 960 | 933 | 935 | 955 | 912 |
| 1059 | 958 | 954 | 1058 | 933 |
| 1072 | 1031 | 1034 | 1077 | 961 |
| 1112 | 1067 | 1059 | 1104 | 1033 |
| 1157 | 1082 | 1075 | 1161 | 1057 |
| 1208 | 1111 | 1103 | 1207 | 1083 |
| 1223 | 1202 | 1161 | 1225 | 1112 |
| 1255 | 1223 | 1206 | 1237 | 1152 |
| 1305 | 1249 |  | 1256 | 1207 |
| 1319 | 1264 | 1237 | 1277 | 1224 |
| 1353 | 1305 | 1253 | 1317 | 1255 |
| 1370 | 1349 | 1278 | 1356 | 1305 |
| 1435 | 1368 | 1319 | 1370 | 1318 |
| 1475 | 1436 | 1355 | 1425 | 1351 |
| 1566 | 1456 | 1370 | 1457 | 1371 |
| 1620 | 1480 | 1424 | 1472 | 1436 |
| 1633 | 1566 | 1437 | 1490 | 1478 |
| 1707 | 1620 | 1458 | 1496 | 1567 |
| 2956 | 1704 | 1476 | 1573 | 1628 |
| 3130 | 2953 | 1489 | 1585 | 1707 |
| 3277 | 3132 | 1570 | 1618 | 2956 |
| 3332 | 3278 | 1587 | 1691 | 3143 |
| 3385 | 3361 | 1619 | 3208 | 3277 |
| 3490 | 3488 | 1695 | 3290 | 3319 |
|  | 3503 | 3203 | 3376 | 3452 |
|  |  | 3315 | 3482 | 3492 |

TABLE 3-continued

IR spectra of polymorphs I to V
Band maxima

| Polymorph I [cm⁻¹] | Polymorph II [cm⁻¹] | Polymorph III [cm⁻¹] | Polymorph IV [cm⁻¹] | Polymorph V [cm⁻¹] |
|---|---|---|---|---|
| | | 3379 | | |
| | | 3479 | | |

TABLE 4

IR spectra of the hydrates and solvates
Band maxima

| Monohydrate [cm⁻¹] | Dihydrate [cm⁻¹] | DMF/water solvate [cm⁻¹] | di-DMSO solvate [cm⁻¹] | Acetic acid solvate [cm⁻¹] |
|---|---|---|---|---|
| 696 | 745 | 662 | 713 | 709 |
| 743 | 752 | 724 | 762 | 739 |
| 761 | 760 | 745 | 778 | 762 |
| 774 | 774 | 771 | 811 | 777 |
| 810 | 809 | 812 | 873 | 801 |
| 834 | 835 | 846 | 902 | 835 |
| 873 | 874 | 867 | 953 | 872 |
| 912 | 913 | 896 | 1017 | 918 |
| 953 | 937 | 932 | 1041 | 941 |
| 1066 | 955 | 965 | 1078 | 955 |
| 1079 | 1032 | 1054 | 1111 | 1059 |
| 1104 | 1061 | 1072 | 1164 | 1099 |
| 1160 | 1080 | 1096 | 1210 | 1113 |
| 1176 | 1105 | 1117 | 1234 | 1167 |
| 1205 | 1160 | 1160 | 1281 | 1236 |
| 1222 | 1174 | 1209 | 1321 | 1252 |
| 1236 | 1206 | 1243 | 1364 | 1357 |
| 1249 | 1224 | 1304 | 1432 | 1423 |
| 1278 | 1236 | 1356 | 1457 | 1456 |
| 1356 | 1259 | 1389 | 1481 | 1492 |
| 1370 | 1309 | 1434 | 1521 | 1577 |
| 1423 | 1356 | 1481 | 1569 | 1601 |
| 1456 | 1371 | 1561 | 1628 | 1643 |
| 1474 | 1422 | 1624 | 1720 | 1702 |
| 1491 | 1473 | 1654 | 3144 | 3342 |
| 1575 | 1497 | 1729 | 3288 | |
| 1620 | 1575 | 3159 | 3423 | |
| 1669 | 1622 | 3404 | | |
| 3294 | 1688 | 3498 | | |
| 3331 | 3195 | | | |
| 3479 | 3304 | | | |
| | 3472 | | | |
| | 3676 | | | |

FIGURES

FIG. 1: IR spectrum of the compound of the formula (I) in polymorphs I, II and III FIG. 2: IR spectrum of the compound of the formula (I) in polymorphs IV, V and as the triacetic acid solvate FIG. 3: IR spectrum of the compound of the formula (I) as the di-DMSO solvate, DMF/water solvate and monohydrate FIG. 4: IR spectrum of the compound of the formula (I) as the dihydrate FIG. 5: X-ray diffractogram of the compound of the formula (I) in polymorph I FIG. 6: X-ray diffractogram of the compound of the formula (I) in polymorph II FIG. 7: X-ray diffractogram of the compound of the formula (I) in polymorph III FIG. 8: X-ray diffractogram of the compound of the formula (I) in polymorph IV FIG. 9: X-ray diffractogram of the compound of the formula (I) in polymorph V FIG. 10: X-ray diffractogram of the compound of the formula (I) as the triacetic acid solvate FIG. 11: X-ray diffractogram of the compound of the formula (I) as the di-DMSO solvate FIG. 12: X-ray diffractogram of the compound of the formula (I) as the DMF-water solvate FIG. 13: X-ray diffractogram of the compound of the formula (I) as the monohydrate FIG. 14: X-ray diffractogram of the compound of the formula (I) as the dihydrate

The invention claimed is:

1. A process of preparing a compound of formula (I), comprising using the compound of formula (VI)

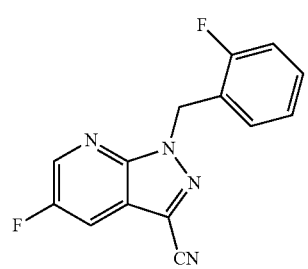

(VI)

to prepare a compound of formula (I)

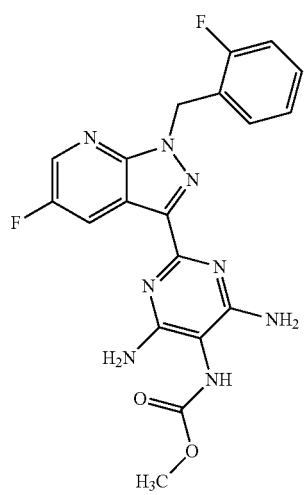

(I)

wherein the compound of formula (I) is optionally converted with an appropriate (i) solvent and/or (ii) acid or base to the solvate, salt and/or solvate of the salt thereof.

2. A process of preparing a compound of formula (I)

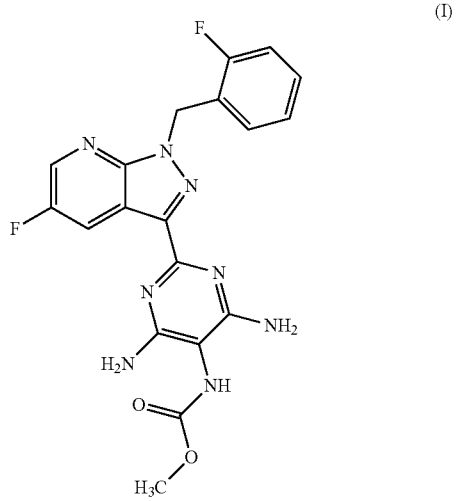 [SMILES: COC(=O)Nc1c(N)nc(-c2nn(Cc3ccccc3F)c3ncc(F)cc23)nc1N]

by converting the compound of the formula (VI) to the compound of the formula (VII)

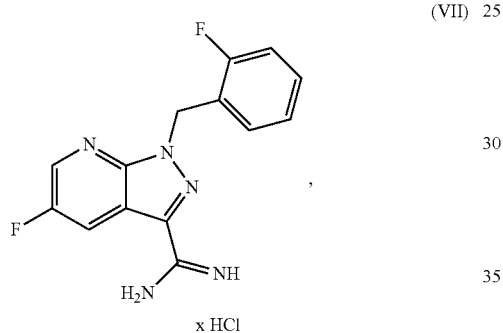

reacting the compound of formula (VII) in an inert solvent in the presence of a suitable base with the compound of the formula (VIIIa)

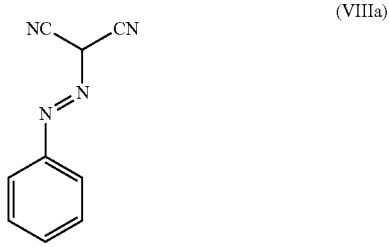 [SMILES: N#CC(C#N)/N=N/c1ccccc1]

to give the compound of the formula (VIII)

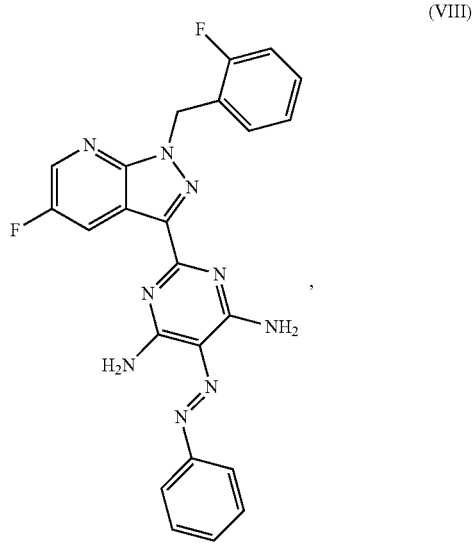 [SMILES: Nc1nc(-c2nn(Cc3ccccc3F)c3ncc(F)cc23)nc(N)c1/N=N/c1ccccc1]

and reducing the compound of formula (VIII) in an inert solvent in the presence of a suitable reducing agent to give the compound (IX)

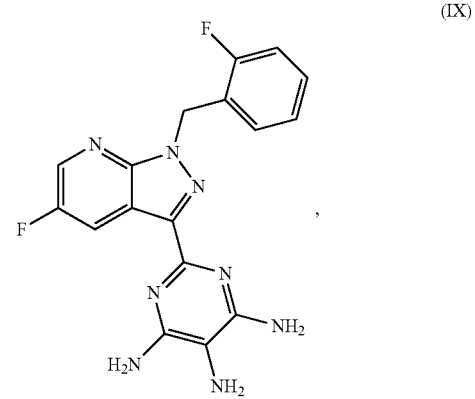 [SMILES: Nc1nc(-c2nn(Cc3ccccc3F)c3ncc(F)cc23)nc(N)c1N]

and reacting the compound of formula (IX) with methyl chloroformate or with dimethyl dicarbonate in the presence of a suitable base with or without solvent to give the compound of the formula (I), and optionally, converting the resulting compound of formula (I) with the appropriate (i) solvent and/or (ii) acid or base to the solvate, salt and/or solvate of the salt thereof.

* * * * *